(12) United States Patent
Sieger et al.

(10) Patent No.: US 9,266,888 B2
(45) Date of Patent: Feb. 23, 2016

(54) POLYMORPHS

(71) Applicants: Peter Sieger, Mittelbiberach (DE); Dirk Kemmer, Windesheim (DE); Peter Kohlbauer, Biberach an der Riss (DE); Thomas Nicola, Ingelheim am Rhein (DE); Martin Renz, Eberhardzell-Dietenwengen (DE)

(72) Inventors: Peter Sieger, Mittelbiberach (DE); Dirk Kemmer, Windesheim (DE); Peter Kohlbauer, Biberach an der Riss (DE); Thomas Nicola, Ingelheim am Rhein (DE); Martin Renz, Eberhardzell-Dietenwengen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 21 days.

(21) Appl. No.: 14/462,654

(22) Filed: Aug. 19, 2014

(65) Prior Publication Data

US 2014/0357646 A1 Dec. 4, 2014

Related U.S. Application Data

(63) Continuation of application No. 13/563,767, filed on Aug. 1, 2012, now abandoned, which is a continuation of application No. 11/744,700, filed on May 4, 2007, now abandoned.

(30) Foreign Application Priority Data

May 4, 2006 (EP) ..................... 06009202

(51) Int. Cl.
*A61K 31/505* (2006.01)
*C07D 473/04* (2006.01)

(52) U.S. Cl.
CPC ..................... *C07D 473/04* (2013.01)

(58) Field of Classification Search
CPC ............... A61K 31/505; C07D 473/04
See application file for complete search history.

(56) References Cited

U.S. PATENT DOCUMENTS

| | | |
|---|---|---|
| 2,056,046 A | 9/1936 | Fourneau |
| 2,375,138 A | 5/1945 | Salvin |
| 2,629,736 A | 2/1953 | Krimmel |
| 2,730,544 A | 1/1956 | Sahyun |
| 2,750,387 A | 6/1956 | Krimmel |
| 2,928,833 A | 3/1960 | Leake et al. |
| 3,174,901 A | 3/1965 | Sterne |
| 3,236,891 A | 2/1966 | Seemuller |
| 3,454,635 A | 7/1969 | Muth |
| 3,673,241 A | 6/1972 | Marxer |
| 3,925,357 A | 12/1975 | Okada et al. |
| 4,005,208 A | 1/1977 | Bender et al. |
| 4,061,753 A | 12/1977 | Bodor et al. |
| 4,382,091 A | 5/1983 | Benjamin et al. |
| 4,599,338 A | 7/1986 | Regnier et al. |
| 4,639,436 A | 1/1987 | Junge et al. |
| 4,687,777 A | 8/1987 | Meguro et al. |
| 4,743,450 A | 5/1988 | Harris et al. |
| 4,816,455 A | 3/1989 | Schickaneder et al. |
| 4,873,330 A | 10/1989 | Lindholm |
| 4,968,672 A | 11/1990 | Jacobson et al. |
| 5,041,448 A | 8/1991 | Janssens et al. |
| 5,051,517 A | 9/1991 | Findeisen et al. |
| 5,084,460 A | 1/1992 | Munson, Jr. et al. |
| 5,130,244 A | 7/1992 | Nishimaki et al. |
| 5,164,526 A | 11/1992 | Macher |
| 5,219,870 A | 6/1993 | Kim |
| 5,223,499 A | 6/1993 | Greenlee et al. |
| 5,234,897 A | 8/1993 | Findeisen et al. |
| 5,258,380 A | 11/1993 | Janssens et al. |
| 5,266,555 A | 11/1993 | Findeisen et al. |
| 5,273,995 A | 12/1993 | Roth |
| 5,284,967 A | 2/1994 | Macher |
| 5,300,298 A | 4/1994 | LaNoue |
| 5,329,025 A | 7/1994 | Wong et al. |
| 5,332,744 A | 7/1994 | Chakravarty et al. |
| 5,389,642 A | 2/1995 | Dorsch et al. |
| 5,399,578 A | 3/1995 | Buhlmayer et al. |
| 5,407,929 A | 4/1995 | Takahashi et al. |
| 5,461,066 A | 10/1995 | Gericke et al. |
| 5,470,579 A | 11/1995 | Bonte et al. |
| 5,591,762 A | 1/1997 | Hauel et al. |
| 5,594,003 A | 1/1997 | Hauel et al. |
| 5,602,127 A | 2/1997 | Hauel et al. |
| 5,614,519 A | 3/1997 | Hauel et al. |
| 5,719,279 A | 2/1998 | Kufner-Muhl et al. |
| 5,728,849 A | 3/1998 | Bouchard et al. |
| 5,753,635 A | 5/1998 | Buckman et al. |
| 5,830,908 A | 11/1998 | Grunenberg et al. |
| 5,879,708 A | 3/1999 | Makino et al. |
| 5,958,951 A | 9/1999 | Ahrndt et al. |

(Continued)

FOREIGN PATENT DOCUMENTS

| | | |
|---|---|---|
| AU | 2003280680 A1 | 6/2004 |
| AU | 2009224546 A1 | 9/2009 |

(Continued)

OTHER PUBLICATIONS

Plummer, C.J.G., et al. "The effect of melting point distributions on DSC melting peaks." Polymer Bulletin. (1996), vol. 36, pp. 355-360.*

(Continued)

Primary Examiner — Noble Jarrell
Assistant Examiner — John S Kenyon
(74) Attorney, Agent, or Firm — Michael P. Morris; David L. Kershner

(57) ABSTRACT

The invention relates to polymorphous crystal modifications of a DPP-IV inhibitor, the preparation thereof and the use thereof for preparing a medicament.

12 Claims, 6 Drawing Sheets

(56) References Cited

U.S. PATENT DOCUMENTS

| | | |
|---|---|---|
| 5,965,555 A | 10/1999 | Gebert et al. |
| 5,965,592 A | 10/1999 | Buhlmayer et al. |
| 6,011,049 A | 1/2000 | Whitcomb |
| 6,107,302 A | 8/2000 | Carter et al. |
| 6,166,063 A | 12/2000 | Villhauer |
| 6,248,758 B1 | 6/2001 | Klokkers et al. |
| 6,303,661 B1 | 10/2001 | Demuth et al. |
| 6,342,601 B1 | 1/2002 | Bantick et al. |
| 6,372,940 B1 | 4/2002 | Cavazza |
| 6,548,481 B1 | 4/2003 | Demuth et al. |
| 6,579,868 B1 | 6/2003 | Asano et al. |
| 6,727,261 B2 | 4/2004 | Gobbi et al. |
| 6,784,195 B2 | 8/2004 | Hale et al. |
| 6,821,978 B2 | 11/2004 | Chackalamannil et al. |
| 6,869,947 B2 | 3/2005 | Kanstrup et al. |
| 6,995,183 B2 | 2/2006 | Hamann et al. |
| 7,060,722 B2 | 6/2006 | Kitajima et al. |
| 7,074,794 B2 | 7/2006 | Kitajima et al. |
| 7,074,798 B2 | 7/2006 | Yoshikawa et al. |
| 7,074,923 B2 | 7/2006 | Dahanukar et al. |
| 7,109,192 B2 | 9/2006 | Hauel et al. |
| 7,179,809 B2 | 2/2007 | Eckhardt et al. |
| 7,183,280 B2 | 2/2007 | Himmelsbach et al. |
| 7,192,952 B2 | 3/2007 | Kanstrup et al. |
| 7,217,711 B2 | 5/2007 | Eckhardt et al. |
| 7,235,538 B2 | 6/2007 | Kanstrup et al. |
| 7,247,478 B2 | 7/2007 | Eberhardt et al. |
| 7,291,642 B2 | 11/2007 | Kauffmann-Hefner et al. |
| 7,361,687 B2 | 4/2008 | Barth et al. |
| 7,393,847 B2 | 7/2008 | Eckhardt et al. |
| 7,407,955 B2 | 8/2008 | Himmelsbach et al. |
| 7,407,995 B2 | 8/2008 | Ok et al. |
| 7,432,262 B2 | 10/2008 | Eckhardt et al. |
| 7,439,370 B2 | 10/2008 | Eckhardt |
| 7,470,716 B2 | 12/2008 | Eckhardt et al. |
| 7,476,671 B2 | 1/2009 | Eckhardt et al. |
| 7,482,337 B2 | 1/2009 | Himmelsbach et al. |
| 7,495,002 B2 | 2/2009 | Langkopf et al. |
| 7,495,003 B2 | 2/2009 | Eckhardt et al. |
| 7,495,005 B2 | 2/2009 | Himmelsbach et al. |
| 7,501,426 B2 | 3/2009 | Himmelsbach et al. |
| 7,550,455 B2 | 6/2009 | Himmelsbach et al. |
| 7,560,450 B2 | 7/2009 | Eckhardt et al. |
| 7,566,707 B2 | 7/2009 | Eckhardt et al. |
| 7,569,574 B2 | 8/2009 | Maier et al. |
| 7,579,449 B2 | 8/2009 | Eckhardt et al. |
| 7,610,153 B2 | 10/2009 | Carter, Jr. et al. |
| 7,645,763 B2 | 1/2010 | Himmelsbach et al. |
| 7,718,666 B2 | 5/2010 | Boehringer et al. |
| 7,754,481 B2 | 7/2010 | Eberhardt et al. |
| 7,799,782 B2 | 9/2010 | Munson et al. |
| 7,820,815 B2 | 10/2010 | Pfrengle et al. |
| 7,838,529 B2 | 11/2010 | Himmelsbach et al. |
| 8,039,477 B2 | 10/2011 | Hendrix et al. |
| 8,071,583 B2 | 12/2011 | Himmelsbach |
| 8,106,060 B2 | 1/2012 | Pfrengle et al. |
| 8,119,648 B2 | 2/2012 | Himmelsbach et al. |
| 8,158,633 B2 | 4/2012 | Hendrix et al. |
| 8,178,541 B2 | 5/2012 | Himmelsbach et al. |
| 8,232,281 B2 | 7/2012 | Dugi et al. |
| 8,673,927 B2 | 3/2014 | Dugi et al. |
| 8,679,520 B2 | 3/2014 | Horres et al. |
| 8,785,455 B2 | 7/2014 | Hotter et al. |
| 8,865,729 B2 | 10/2014 | Sieger et al. |
| 8,962,636 B2 | 2/2015 | Pfrengle et al. |
| 2001/0020006 A1 | 9/2001 | Demuth et al. |
| 2001/0051646 A1 | 12/2001 | Demuth et al. |
| 2002/0019411 A1 | 2/2002 | Robl et al. |
| 2002/0137903 A1 | 9/2002 | Ellsworth et al. |
| 2002/0161001 A1 | 10/2002 | Kanstrup et al. |
| 2002/0169174 A1 | 11/2002 | Chackalamannil et al. |
| 2002/0198205 A1 | 12/2002 | Himmelsbach et al. |
| 2003/0078269 A1 | 4/2003 | Pearson et al. |
| 2003/0100563 A1 | 5/2003 | Edmondson et al. |
| 2003/0105077 A1 | 6/2003 | Kanstrup et al. |
| 2003/0114390 A1 | 6/2003 | Washburn et al. |
| 2003/0130313 A1 | 7/2003 | Fujino et al. |
| 2003/0149071 A1 | 8/2003 | Gobbi et al. |
| 2003/0166578 A1 | 9/2003 | Arch et al. |
| 2003/0199528 A1 | 10/2003 | Kanstrup et al. |
| 2003/0224043 A1 | 12/2003 | Appel et al. |
| 2003/0232987 A1 | 12/2003 | Dahanukar et al. |
| 2003/0236272 A1 | 12/2003 | Carr |
| 2004/0023981 A1 | 2/2004 | Ren et al. |
| 2004/0034014 A1 | 2/2004 | Kanstrup et al. |
| 2004/0063725 A1 | 4/2004 | Barth et al. |
| 2004/0077645 A1 | 4/2004 | Himmelsbach et al. |
| 2004/0082570 A1 | 4/2004 | Yoshikawa et al. |
| 2004/0087587 A1 | 5/2004 | Himmelsbach et al. |
| 2004/0097510 A1* | 5/2004 | Himmelsbach et al. ...... 514/248 |
| 2004/0116328 A1 | 6/2004 | Yoshikawa et al. |
| 2004/0122048 A1 | 6/2004 | Benjamin et al. |
| 2004/0122228 A1 | 6/2004 | Maier et al. |
| 2004/0126358 A1 | 7/2004 | Warne et al. |
| 2004/0138214 A1 | 7/2004 | Himmelsbach et al. |
| 2004/0138215 A1 | 7/2004 | Eckhardt et al. |
| 2004/0152720 A1 | 8/2004 | Hartig et al. |
| 2004/0166125 A1 | 8/2004 | Himmelsbach et al. |
| 2004/0171836 A1 | 9/2004 | Fujino et al. |
| 2004/0180925 A1 | 9/2004 | Matsuno et al. |
| 2004/0259903 A1 | 12/2004 | Boehringer et al. |
| 2005/0020574 A1 | 1/2005 | Hauel et al. |
| 2005/0026921 A1 | 2/2005 | Eckhardt et al. |
| 2005/0032804 A1 | 2/2005 | Cypes et al. |
| 2005/0065145 A1 | 3/2005 | Cao et al. |
| 2005/0070562 A1 | 3/2005 | Jones et al. |
| 2005/0070594 A1 | 3/2005 | Kauschke et al. |
| 2005/0130985 A1 | 6/2005 | Himmelsbach et al. |
| 2005/0143377 A1 | 6/2005 | Himmelsbach et al. |
| 2005/0171093 A1 | 8/2005 | Eckhardt et al. |
| 2005/0187227 A1 | 8/2005 | Himmelsbach et al. |
| 2005/0203095 A1 | 9/2005 | Eckhardt et al. |
| 2005/0234108 A1 | 10/2005 | Himmelsbach et al. |
| 2005/0234235 A1 | 10/2005 | Eckhardt et al. |
| 2005/0239778 A1 | 10/2005 | Konetzki et al. |
| 2005/0244502 A1 | 11/2005 | Mathias et al. |
| 2005/0256310 A1 | 11/2005 | Hulin et al. |
| 2005/0261271 A1 | 11/2005 | Feng et al. |
| 2005/0261352 A1 | 11/2005 | Eckhardt |
| 2005/0266080 A1 | 12/2005 | Desai et al. |
| 2005/0276794 A1 | 12/2005 | Papas et al. |
| 2006/0004074 A1 | 1/2006 | Eckhardt et al. |
| 2006/0034922 A1 | 2/2006 | Cheng et al. |
| 2006/0039974 A1 | 2/2006 | Akiyama et al. |
| 2006/0047125 A1 | 3/2006 | Leonardi et al. |
| 2006/0058323 A1 | 3/2006 | Eckhardt et al. |
| 2006/0063787 A1 | 3/2006 | Yoshikawa et al. |
| 2006/0074058 A1 | 4/2006 | Holmes et al. |
| 2006/0079541 A1 | 4/2006 | Langkopf et al. |
| 2006/0094722 A1 | 5/2006 | Yasuda et al. |
| 2006/0100199 A1 | 5/2006 | Yoshikawa et al. |
| 2006/0106035 A1 | 5/2006 | Hendrix et al. |
| 2006/0111372 A1 | 5/2006 | Hendrix et al. |
| 2006/0111379 A1 | 5/2006 | Guillemont et al. |
| 2006/0134206 A1 | 6/2006 | Iyer et al. |
| 2006/0142310 A1 | 6/2006 | Pfrengle et al. |
| 2006/0154866 A1 | 7/2006 | Chu et al. |
| 2006/0159746 A1 | 7/2006 | Troup et al. |
| 2006/0173056 A1 | 8/2006 | Kitajima et al. |
| 2006/0205711 A1 | 9/2006 | Himmelsbach et al. |
| 2006/0205943 A1 | 9/2006 | Dahanukar et al. |
| 2006/0247226 A1 | 11/2006 | Himmelsbach et al. |
| 2006/0270668 A1 | 11/2006 | Chew et al. |
| 2006/0270701 A1 | 11/2006 | Kroth et al. |
| 2007/0027168 A1 | 2/2007 | Pfrengle et al. |
| 2007/0060530 A1 | 3/2007 | Christopher et al. |
| 2007/0072803 A1 | 3/2007 | Chu et al. |
| 2007/0072810 A1 | 3/2007 | Asakawa |
| 2007/0088038 A1 | 4/2007 | Eckhardt et al. |
| 2007/0093659 A1 | 4/2007 | Bonfanti et al. |
| 2007/0142383 A1 | 6/2007 | Eckhardt et al. |
| 2007/0185091 A1 | 8/2007 | Himmelsbach et al. |
| 2007/0196472 A1 | 8/2007 | Kiel et al. |
| 2007/0197522 A1 | 8/2007 | Edwards et al. |

(56) References Cited

U.S. PATENT DOCUMENTS

| | | |
|---|---|---|
| 2007/0219178 A1 | 9/2007 | Muramoto |
| 2007/0259900 A1 | 11/2007 | Sieger et al. |
| 2007/0259925 A1 | 11/2007 | Boehringer et al. |
| 2007/0259927 A1 | 11/2007 | Suzuki et al. |
| 2007/0281940 A1 | 12/2007 | Dugi et al. |
| 2007/0299076 A1 | 12/2007 | Piotrowski et al. |
| 2008/0039427 A1 | 2/2008 | Ray et al. |
| 2008/0107731 A1 | 5/2008 | Kohlrausch et al. |
| 2008/0108816 A1 | 5/2008 | Zutter |
| 2008/0249089 A1 | 10/2008 | Himmelsbach et al. |
| 2008/0255159 A1 | 10/2008 | Himmelsbach et al. |
| 2008/0312243 A1 | 12/2008 | Eckhardt et al. |
| 2008/0318922 A1 | 12/2008 | Nakahira et al. |
| 2009/0023920 A1 | 1/2009 | Eckhardt |
| 2009/0088408 A1 | 4/2009 | Meade et al. |
| 2009/0088569 A1 | 4/2009 | Eckhardt et al. |
| 2009/0093457 A1 | 4/2009 | Himmelsbach et al. |
| 2009/0131432 A1 | 5/2009 | Himmelsbach et al. |
| 2009/0136596 A1 | 5/2009 | Munson et al. |
| 2009/0137801 A1 | 5/2009 | Himmelsbach et al. |
| 2009/0149483 A1 | 6/2009 | Nakahira et al. |
| 2009/0186086 A1 | 7/2009 | Shankar et al. |
| 2009/0192314 A1 | 7/2009 | Pfrengle et al. |
| 2009/0297470 A1 | 12/2009 | Franz |
| 2009/0301105 A1 | 12/2009 | Loerting |
| 2009/0325926 A1 | 12/2009 | Himmelsbach |
| 2010/0074950 A1 | 3/2010 | Sesha |
| 2010/0092551 A1 | 4/2010 | Nakamura et al. |
| 2010/0173916 A1 | 7/2010 | Himmelsbach et al. |
| 2010/0179191 A1 | 7/2010 | Himmelsbach et al. |
| 2010/0183531 A1 | 7/2010 | Johncock et al. |
| 2010/0204250 A1 | 8/2010 | Himmelsbach et al. |
| 2010/0209506 A1 | 8/2010 | Eisenreich |
| 2010/0310664 A1 | 12/2010 | Watson et al. |
| 2011/0009391 A1 | 1/2011 | Braun et al. |
| 2011/0046076 A1 | 2/2011 | Eickelmann et al. |
| 2011/0065731 A1 | 3/2011 | Dugi et al. |
| 2011/0092510 A1 | 4/2011 | Klein et al. |
| 2011/0098240 A1 | 4/2011 | Dugi et al. |
| 2011/0112069 A1 | 5/2011 | Himmelsbach et al. |
| 2011/0144083 A1 | 6/2011 | Himmelsbach et al. |
| 2011/0144095 A1 | 6/2011 | Himmelsbach et al. |
| 2011/0190322 A1 | 8/2011 | Klein et al. |
| 2011/0195917 A1 | 8/2011 | Dugi et al. |
| 2011/0206766 A1 | 8/2011 | Friedl et al. |
| 2011/0263493 A1 | 10/2011 | Dugi et al. |
| 2011/0263617 A1 | 10/2011 | Mark et al. |
| 2011/0275561 A1 | 11/2011 | Graefe-Mody et al. |
| 2011/0301182 A1 | 12/2011 | Dugi |
| 2012/0003313 A1 | 1/2012 | Kohlrausch et al. |
| 2012/0035158 A1 | 2/2012 | Himmelsbach et al. |
| 2012/0040982 A1 | 2/2012 | Himmelsbach et al. |
| 2012/0053173 A1 | 3/2012 | Banno et al. |
| 2012/0094894 A1 | 4/2012 | Graefe-Mody et al. |
| 2012/0107398 A1 | 5/2012 | Schneider et al. |
| 2012/0121530 A1 | 5/2012 | Klein et al. |
| 2012/0122776 A1 | 5/2012 | Graefe-Mody et al. |
| 2012/0129874 A1 | 5/2012 | Sieger et al. |
| 2012/0142712 A1 | 6/2012 | Pfrengle et al. |
| 2012/0165251 A1 | 6/2012 | Klein et al. |
| 2012/0208831 A1 | 8/2012 | Himmelsbach et al. |
| 2012/0219622 A1 | 8/2012 | Kohlrausch et al. |
| 2012/0219623 A1 | 8/2012 | Meinicke |
| 2012/0252782 A1 | 10/2012 | Himmelsbach et al. |
| 2012/0252783 A1 | 10/2012 | Himmelsbach et al. |
| 2012/0296091 A1 | 11/2012 | Sieger et al. |
| 2013/0122089 A1 | 5/2013 | Kohlrausch et al. |
| 2013/0172244 A1 | 7/2013 | Klein et al. |
| 2013/0184204 A1 | 7/2013 | Pfrengle et al. |
| 2013/0196898 A1 | 8/2013 | Dugi et al. |
| 2013/0236543 A1 | 9/2013 | Ito et al. |

FOREIGN PATENT DOCUMENTS

| | | |
|---|---|---|
| CA | 1123437 A1 | 5/1982 |
| CA | 2136288 A1 | 5/1995 |
| CA | 2418656 A1 | 2/2002 |
| CA | 2435730 A1 | 9/2002 |
| CA | 2496249 A1 | 3/2004 |
| CA | 2496325 A1 | 3/2004 |
| CA | 2498423 A1 | 4/2004 |
| CA | 2505389 A1 | 5/2004 |
| CA | 2508233 A1 | 6/2004 |
| CA | 2529729 A1 | 12/2004 |
| CA | 2543074 A1 | 6/2005 |
| CA | 2555050 A1 | 9/2005 |
| CA | 2556064 A1 | 9/2005 |
| CA | 2558067 A1 | 10/2005 |
| CA | 2561210 A1 | 10/2005 |
| CA | 2562859 A1 | 11/2005 |
| CA | 2576294 A1 | 3/2006 |
| CA | 2590912 A1 | 6/2006 |
| CA | 2651019 A1 | 11/2007 |
| CA | 2651089 A1 | 11/2007 |
| CN | 101234105 A | 8/2008 |
| DE | 2205815 A1 | 8/1973 |
| DE | 2758025 A1 | 7/1979 |
| DE | 10109021 A1 | 9/2002 |
| DE | 10117803 A1 | 10/2002 |
| DE | 10238243 A1 | 3/2004 |
| DE | 102004019540 A1 | 11/2005 |
| DE | 102004024454 A1 | 12/2005 |
| DE | 102004044221 A1 | 3/2006 |
| DE | 102004054054 A1 | 5/2006 |
| EP | 0023032 A1 | 1/1981 |
| EP | 0149578 A2 | 7/1985 |
| EP | 0223403 A2 | 5/1987 |
| EP | 0237608 A1 | 9/1987 |
| EP | 0248634 A2 | 12/1987 |
| EP | 0342675 A2 | 11/1989 |
| EP | 0389282 A2 | 9/1990 |
| EP | 0399285 A1 | 11/1990 |
| EP | 0400974 A2 | 12/1990 |
| EP | 409281 A1 | 1/1991 |
| EP | 0412358 A1 | 2/1991 |
| EP | 443983 A1 | 8/1991 |
| EP | 0475482 A1 | 3/1992 |
| EP | 0524482 A1 | 1/1993 |
| EP | 0657454 A1 | 6/1995 |
| EP | 0775704 A1 | 5/1997 |
| EP | 0950658 A1 | 10/1999 |
| EP | 1054012 A1 | 11/2000 |
| EP | 1066265 A1 | 1/2001 |
| EP | 1310245 A1 | 5/2003 |
| EP | 1333033 | 8/2003 |
| EP | 1338595 A2 | 8/2003 |
| EP | 1406873 A2 | 4/2004 |
| EP | 1500403 A1 | 1/2005 |
| EP | 1514552 A1 | 3/2005 |
| EP | 1535906 A1 | 6/2005 |
| EP | 1537880 A1 | 6/2005 |
| EP | 1557165 A1 | 7/2005 |
| EP | 1586571 A1 | 10/2005 |
| EP | 1743655 A1 | 1/2007 |
| EP | 1760076 | 3/2007 |
| EP | 1829877 A1 | 9/2007 |
| EP | 1852108 A1 | 11/2007 |
| EP | 1897892 A2 | 3/2008 |
| EP | 2143443 A1 | 1/2010 |
| ES | 385302 A1 | 4/1973 |
| ES | 2256797 T3 | 7/2006 |
| ES | 2263057 T3 | 12/2006 |
| FR | 2707641 A1 | 1/1995 |
| GB | 2084580 A | 4/1982 |
| HU | 9003243 | 5/1990 |
| HU | 9902308 A2 | 7/2000 |
| JP | S374895 A | 6/1962 |
| JP | 770120 | 3/1995 |
| JP | 8333339 | 12/1996 |
| JP | 11193270 | 7/1999 |
| JP | 2000502684 A | 3/2000 |

(56) References Cited

FOREIGN PATENT DOCUMENTS

| | | | |
|---|---|---|---|
| JP | 2001213770 A | 8/2001 |
| JP | 2001278812 A | 10/2001 |
| JP | 2002348279 A | 12/2002 |
| JP | 2003286287 A | 10/2003 |
| JP | 2003300977 A | 10/2003 |
| JP | 2004161749 A | 6/2004 |
| JP | 2004250336 A | 9/2004 |
| JP | 2006045156 A | 2/2006 |
| JP | 2010053576 A | 3/2010 |
| JP | 2010070576 A | 4/2010 |
| JP | 2010524580 A | 7/2010 |
| KR | 20070111099 A | 11/2007 |
| WO | 9107945 A1 | 6/1991 |
| WO | 9205175 A1 | 4/1992 |
| WO | 9219227 A2 | 11/1992 |
| WO | 9402150 A1 | 2/1994 |
| WO | 9403456 A1 | 2/1994 |
| WO | 9532178 A1 | 11/1995 |
| WO | 9609045 A1 | 3/1996 |
| WO | 9611917 A1 | 4/1996 |
| WO | 9636638 A1 | 11/1996 |
| WO | 9723447 A1 | 7/1997 |
| WO | 9723473 A1 | 7/1997 |
| WO | 9746526 A1 | 12/1997 |
| WO | 9807725 | 2/1998 |
| WO | 9811893 | 3/1998 |
| WO | 9818770 A1 | 5/1998 |
| WO | 9822464 A1 | 5/1998 |
| WO | 9828007 A1 | 7/1998 |
| WO | 9840069 A2 | 9/1998 |
| WO | 9846082 A1 | 10/1998 |
| WO | 9856406 A1 | 12/1998 |
| WO | 9929695 A1 | 6/1999 |
| WO | 9938501 A2 | 8/1999 |
| WO | 9950248 A1 | 10/1999 |
| WO | 9956561 A1 | 11/1999 |
| WO | 9967279 A1 | 12/1999 |
| WO | 0073307 A2 | 12/2000 |
| WO | 0107441 A1 | 2/2001 |
| WO | 0140180 A2 | 6/2001 |
| WO | 0151919 | 7/2001 |
| WO | 0152825 | 7/2001 |
| WO | 0152825 A2 | 7/2001 |
| WO | 0152852 A1 | 7/2001 |
| WO | 0166548 A1 | 9/2001 |
| WO | 0168646 A1 | 9/2001 |
| WO | 0172290 A2 | 10/2001 |
| WO | 0177110 A1 | 10/2001 |
| WO | 0196301 A1 | 12/2001 |
| WO | 0197808 A1 | 12/2001 |
| WO | 0202560 A2 | 1/2002 |
| WO | 0214271 A1 | 2/2002 |
| WO | 0224698 A1 | 3/2002 |
| WO | 02053516 A2 | 7/2002 |
| WO | 02068420 A1 | 9/2002 |
| WO | 03000241 A2 | 1/2003 |
| WO | 03002531 A2 | 1/2003 |
| WO | 03004496 A1 | 1/2003 |
| WO | 03024965 A2 | 3/2003 |
| WO | 03033686 A2 | 4/2003 |
| WO | 03034944 A1 | 5/2003 |
| WO | 03037327 A1 | 5/2003 |
| WO | 03053929 A1 | 7/2003 |
| WO | 03055881 A1 | 7/2003 |
| WO | 03057200 A2 | 7/2003 |
| WO | 03064454 A1 | 8/2003 |
| WO | 03088900 A2 | 10/2003 |
| WO | 03094909 A2 | 11/2003 |
| WO | 03099279 A1 | 12/2003 |
| WO | 03099836 A1 | 12/2003 |
| WO | 03103629 A1 | 12/2003 |
| WO | 03104229 A1 | 12/2003 |
| WO | 03106428 A1 | 12/2003 |
| WO | 2004002924 A1 | 1/2004 |
| WO | 2004011416 A1 | 2/2004 |
| WO | 2004016587 A1 | 2/2004 |
| WO | 2004018467 A2 | 3/2004 |
| WO | 2004018468 A2 | 3/2004 |
| WO | 2004018469 A1 | 3/2004 |
| WO | 2004028524 A1 | 4/2004 |
| WO | 2004033455 A1 | 4/2004 |
| WO | 2004035575 A1 | 4/2004 |
| WO | 2004041820 A1 | 5/2004 |
| WO | 2004046148 A1 | 6/2004 |
| WO | 2004048379 A1 | 6/2004 |
| WO | 2004050658 A1 | 6/2004 |
| WO | 2004052362 A1 | 6/2004 |
| WO | 2004058233 A1 | 7/2004 |
| WO | 2004062689 A1 | 7/2004 |
| WO | 2004065380 A1 | 8/2004 |
| WO | 2004074246 A2 | 9/2004 |
| WO | 2004081006 A1 | 9/2004 |
| WO | 2004082402 A1 | 9/2004 |
| WO | 2004096806 A1 | 11/2004 |
| WO | 2004096811 A1 | 11/2004 |
| WO | 2004106279 A2 | 12/2004 |
| WO | 2004108730 A1 | 12/2004 |
| WO | 2004111051 A1 | 12/2004 |
| WO | 2005000846 A1 | 1/2005 |
| WO | 2005000848 A1 | 1/2005 |
| WO | 2005007647 A1 | 1/2005 |
| WO | 2005007658 A2 | 1/2005 |
| WO | 2005012288 A1 | 2/2005 |
| WO | 2005023179 A2 | 3/2005 |
| WO | 2005049022 A2 | 6/2005 |
| WO | 2005051950 A1 | 6/2005 |
| WO | 2005058901 A1 | 6/2005 |
| WO | 2005061489 A1 | 7/2005 |
| WO | 2005063750 A1 | 7/2005 |
| WO | 2005082906 A1 | 9/2005 |
| WO | 2005085246 A1 | 9/2005 |
| WO | 2005092870 A1 | 10/2005 |
| WO | 2005092877 A1 | 10/2005 |
| WO | 2005095343 A1 | 10/2005 |
| WO | 2005095381 A1 | 10/2005 |
| WO | 2005097798 A | 10/2005 |
| WO | 2005116000 A1 | 12/2005 |
| WO | 2005116014 A1 | 12/2005 |
| WO | 2005117861 A1 | 12/2005 |
| WO | 2005117948 A1 | 12/2005 |
| WO | 2006005613 A1 | 1/2006 |
| WO | 2006027204 A1 | 3/2006 |
| WO | 2006029577 A1 | 3/2006 |
| WO | 2006029769 A1 | 3/2006 |
| WO | 2006036664 A1 | 4/2006 |
| WO | 2006040625 A1 | 4/2006 |
| WO | 2006041976 A1 | 4/2006 |
| WO | 2006047248 A1 | 5/2006 |
| WO | 2006048209 A1 | 5/2006 |
| WO | 2006048427 A1 | 5/2006 |
| WO | 2006068163 A1 | 6/2006 |
| WO | 2006071078 A1 | 7/2006 |
| WO | 2006076231 A2 | 7/2006 |
| WO | 2006083491 A2 | 8/2006 |
| WO | 2006135693 A2 | 12/2006 |
| WO | 2006137085 A1 | 12/2006 |
| WO | 2007007173 A2 | 1/2007 |
| WO | 2007014886 A1 | 2/2007 |
| WO | 2007014895 A2 | 2/2007 |
| WO | 2007017423 A1 | 2/2007 |
| WO | 2007033350 A1 | 3/2007 |
| WO | 2007035355 A2 | 3/2007 |
| WO | 2007035665 A1 | 3/2007 |
| WO | 2007041053 A2 | 4/2007 |
| WO | 2007071738 | 6/2007 |
| WO | 2007072083 A1 | 6/2007 |
| WO | 2007078726 A1 | 7/2007 |
| WO | 2007093610 A1 | 8/2007 |
| WO | 2007099345 A1 | 9/2007 |
| WO | 2007120702 A2 | 10/2007 |
| WO | 2007120936 A2 | 10/2007 |
| WO | 2007128721 A | 11/2007 |
| WO | 2007128724 A1 | 11/2007 |
| WO | 2007128761 A2 | 11/2007 |

(56) References Cited

FOREIGN PATENT DOCUMENTS

| | | |
|---|---|---|
| WO | 2007135196 A2 | 11/2007 |
| WO | 2007137107 A2 | 11/2007 |
| WO | 2007147185 A1 | 12/2007 |
| WO | 2007148185 A2 | 12/2007 |
| WO | 2007149797 A2 | 12/2007 |
| WO | 2008005569 A2 | 1/2008 |
| WO | 2008005576 A1 | 1/2008 |
| WO | 2008017670 | 2/2008 |
| WO | 2008022267 A2 | 2/2008 |
| WO | 2008055870 A1 | 5/2008 |
| WO | 2008055940 A2 | 5/2008 |
| WO | 2008070692 A2 | 6/2008 |
| WO | 2008081205 A1 | 7/2008 |
| WO | 2008083238 A2 | 7/2008 |
| WO | 2008087198 A1 | 7/2008 |
| WO | 2008093878 A1 | 8/2008 |
| WO | 2008093882 A1 | 8/2008 |
| WO | 2008113000 A1 | 9/2008 |
| WO | 2008130998 A2 | 10/2008 |
| WO | 2008131149 A2 | 10/2008 |
| WO | 2008137435 A1 | 11/2008 |
| WO | 2009011451 A | 1/2009 |
| WO | 2009022007 A1 | 2/2009 |
| WO | 2009022008 A1 | 2/2009 |
| WO | 2009022009 A1 | 2/2009 |
| WO | 2009022010 A1 | 2/2009 |
| WO | 2009024542 A2 | 2/2009 |
| WO | 2009063072 A2 | 5/2009 |
| WO | 2009099734 A1 | 8/2009 |
| WO | 2009112691 A2 | 9/2009 |
| WO | 2009121945 A2 | 10/2009 |
| WO | 2009123992 A1 | 10/2009 |
| WO | 2009147125 A1 | 12/2009 |
| WO | 2010015664 A1 | 2/2010 |
| WO | 2010018217 A2 | 2/2010 |
| WO | 2010029089 A2 | 3/2010 |
| WO | 2010043688 A1 | 4/2010 |
| WO | 2010045656 A2 | 4/2010 |
| WO | 2010072776 A1 | 7/2010 |
| WO | 2010079197 A1 | 7/2010 |
| WO | 2010086411 A1 | 8/2010 |
| WO | 2010092124 A1 | 8/2010 |
| WO | 2010092125 A1 | 8/2010 |
| WO | 2010092163 A2 | 8/2010 |
| WO | 2010096384 A2 | 8/2010 |
| WO | 2010106457 A2 | 9/2010 |
| WO | 2010147768 A1 | 12/2010 |
| WO | 2011011541 A1 | 1/2011 |
| WO | 2011039337 A1 | 4/2011 |
| WO | 2011039367 A2 | 4/2011 |
| WO | 2011064352 A1 | 6/2011 |
| WO | 2011113947 A1 | 9/2011 |
| WO | 2011138380 A1 | 11/2011 |
| WO | 2011138421 A1 | 11/2011 |
| WO | 2011161161 A1 | 12/2011 |
| WO | 2012031124 A2 | 3/2012 |
| WO | 2012065993 A1 | 5/2012 |
| WO | 2012106303 A1 | 8/2012 |
| WO | 2012120040 A1 | 9/2012 |
| WO | 2013098372 A1 | 7/2013 |
| WO | 2013103629 A1 | 7/2013 |
| WO | 2013171167 A1 | 11/2013 |
| WO | 2013174768 A1 | 11/2013 |

OTHER PUBLICATIONS

Knorr, M. et al., "Comparison of Direct and Indirect Antioxidant Effects of Linagliptin (BI 1356, Ondero) with other Gliptins—Evidence for Anti-Inflammatory Properties of Linagliptin". Free Radical Biology and medicine, Elsevier Science, U.S. vol. 49, Oct. 23, 2010, p. S197.

Komori, Kiyoshi., "Treatment of Diabetes in Patients for Whom Metforming Treatment is Not Appropriate" Modern Physician (2008) vol. 28, No. 2 pp. 163-165.

Korom, S. et al; Inhibition of CD26/dipeptidyl peptidase IV activity in vivo prolongs cardiac allograft survival in rat recipients1,2, Transplantation, May 27, 1997, vol. 63, No. 10, pp. 1495-1500.

Kroller-Schön, S. et al., "Glucose-independent Improvement of Vascular Dysfunction in Experimental Sepsis by Dipeptidyl Peptidase-4 Inhibition." Cardiovascular Research, 2012, vol. 96, No. 1, pp. 140-149.

Lakatos, P. L et al., "Elevated Serum Dipeptidyl IV (CD26, EC 3.4.14.5) Activity in Experimental Liver Cirrhosis." European Journal of Clinical Investigation, 2000, vol. 30, No. 9, pp. 793-797.

Lambier, A.M. et al., Dipeptidyl-Peptidase IV from Bench to Bedside: An Update on Structural Properties, Functions, and Clinical Aspects of the Enzyme DPP IV. Critical Reviews in Clinical Laboratory Sciences, 2003, 40(3), p. 209-294.

Lee Jones, K. et al., "Effect of Metformin in Pediatric Patients With Type 2 Diabetes." Diabetes Care, 2002, vol. 25, No. 1, pp. 89-94.

Leibovitz, Cardiovascular Diabetology, Sitagliptin Treatment in diabetes patients presenting with acute coronary syndrome: results from the Acute Coronary Syndrome Israeli Survey, 2013.

Leibovitz, E. et al., "Sitagliptin pretreatment in diabetes patients presenting with acute coronary syndrome: results from the Acute Coronary Syndrome Israeli Survey (ACSIS)." Cardiovascular Diabetology, 2013, vol. 12, No. 1, pp. 1-7.

Levien,T.L. et al, "New drugs in development for the treatment of diabetes", Diabetes Spectrum, American Diabetes Association, US, vol. 22, No. 2, Jan. 1, 2009, pp. 92-106.

Lim, S. et al., "Effect of a Dipeptidyl Peptidase-IV Inhibitor, Des-Fluoro-Sitagliptin, on Neointimal Formation after Balloon Injury in Rats." Plos One, 2012, vol. 7, No. 4, pp. 1-11.

Lim, Seoul National Univ. Bundang Hospital, Effect of a Dipeptyl Peptidase-IV Inhibitor, Des-Fluoro Sitagliptin, on Neointimal Formation after Balloon Injury in Rats, 2012, vol. 7, Issue 4.

Lovshin, J.A. et al., "Incretin-based therapies for type 2 diabetes mellitus." Nature Reviews Endocrinology, 2009, vol. 5, pp. 262-269.

March, J. "Advanced Organic Chemistry: Reactions, Mechanisms, and Structure". Fourth Edition, 1992, pp. 652-653.

Matsumiya, Teruhiko, et al., "Therapeutic Drugs for Clinicians" Diagnosis and Treatment (2008) vol. 96, No. 2 pp. 389-390.

Matsumiya, Tokyo Medical University, Department of Pharmacology, Diagnosis and Therapy, vol. 96, No. 2, 2008.

Mayo Clinic Staff: "Nonalchoholic fatty liver disease: Prevention" [retrieved on Nov. 30, 2012]. retrieved from the Internet: ,URL: http://www.mayoclinic.com/health/nonalcoholic-fatty-liver-disease/DS00577DSECTION=prevention>.

Medline Plus, "Obesity" 2013, Retrieved from Internet on Aug. 22, 2013, http://www.nlm.nih.gov/medlineplus/obesity.html.

Meece, J. "When Oral Agents Fail: Optimizing Insulin Therapy in the Older Adult". Consultant Pharmacist, The Society, Arlington, VA US. vol. 24, No. Suppl B, Jun. 1, 2009, p. 11-17.

Mendes, F.D, et al. "Recent advances in the treatment of non-alcoholic fatty liver disease". Expert Opinion on Investigational Drugs, vol. 14, No. 1, Jan. 1, 2005, p. 29-35.

Merck: "Initial Therapy with Janumet (sitagliptin/metformin) provided significantly greater blood sugar lowering compared to metformin alone in patients with type 2 diabetes". Webwire.com, Jun. 8, 2009, p. 1-4. http://www.webwire.com/ViewPressRel.asp?aId=96695.

Nathan, D. et al., "Management of Hyperglycemia in Type 2 Diabetes: A Consensus Algorithm for the Initiation and Adjustment of Therapy." Diabetes Care, Aug. 2006, vol. 29, No. 8, pp. 1963-1972.

Nauck, M. A. et al., "Efficacy and Safety of Adding the Dipeptidyl Peptidase-4 Inhibitor Alogliptin to Metformin Therapy in Patients with Type 2 Diabetes Inadequately Controlled with Metformin Monotherapy: A Multicentre, Randomised, Double-Blind, Placebo-Cotrolled Study." Clinical Practice, 2008, vol. 63, No. 1, pp. 46-55.

Nauck, M. A. et al., "Efficacy and Safety of the Dipeptidyl Peptidase-4 Inhibitor, Sitagliptin, Compared with the Sulfonylurea, Glipizide, in Patients with Type 2 Diabetes Inaduately Controlled on Metformin alone: A Randomized, Double-Blind, Non-Inferiority Trial." Diabetes Obesity and Metabolism, 2007, vol. 9, No. 2, pp. 194-205.

Nielsen, L., "Incretin Mimetics and DPP-IV Inhibitors for the Treatment of Type 2 Diabetes." DDT, 2005, vol. 10, No. 10, pp. 703-710.

(56) References Cited

OTHER PUBLICATIONS

Nihon Ijinpo, Japan Medicinal Journal, 2001, No. 4032, p. 137.
Nippon Rinsho, Insulin Glargine, Tokyo Women's Medical Univ. Diabetes Center, 2011.
O'Farrell, et al., "Pharmacokinetic and Pharmacodynamic Assessments of the Dipeptidyl Peptidase-4 Inhibitor PHX1149: Double-Blind, Placebo-controlled, Single-and Multiple-Dose Studies in Healthy Subjects". Clinical Therapeutics, Excerpta Medica, Princeton, NJ, vol. 29, No. 8, 2007, p. 1692-1705.
Office Action for U.S. Appl. No. 10/695,597 mailed May 2, 2008.
Patani George A. et al.: "Bioisoterism : A Rational Approach in Drug Design", Chemical Reviews, 1996, vol. 96, No. 8, pp. 3147-3176.
Pei, Z.: "From the bench to the bedside: Dipeptidyl peptidase IV inhibitors, a new class of oral antihyperglycemic agents" Current Opinion in Drug Discovery and Development, Current Drugs, London, GB vol. 11, No. 4, Jul. 1, 2008 pp. 512-532.
Plummer, C.J.G. et al., "The Effect of Melting Point Distributions on DSC Melting Peaks." Polymer Bulletin, 1996, vol. 36, pp. 355-360.
Pospisilik, et al; Dipeptidyl Peptidase IV Inhibitor Treatment Stimulates ?—Cell Survival and Islet Neogenesis in Streptozotocin-Induced Diabetic Rats; Diabetes, vol. 52, Mar. 2003 pp. 741-750.
Pratley, R. et al., "Inhibition of DPP-4: a new therapeutic approach for the treatment of type 2 diabetes." Current Medical Research and Opinion, 2007, vol. 23, No. 4, pp. 919-931.
Prescribing Information, Package insert for Leprinton tablets 100mg, Manufacturer: Tatsumi Kagaku Co., Ltd., Mar. 2003.
Priimenko, B. A., et al; Synthesis and Pharmacological Activity of Derivates of 6,8-Dimethyl Imidazo(1,2-f) Xanthine-(Russ.); Khimiko-Farmatsevticheskii zhurnal (1984) vol. 18, No. 12 pp. 1456-1461.
Rask-Madsen, C. et al., "Podocytes lose their footing." Nature, 2010, vol. 468, pp. 42-44.
Rhee et al.: "Nitrogen-15-Labeled Deoxynucleosides. 3. Synthesis of [3-15N]-2'-Deoxyadenosine" J. Am. Chem. Soc. 1990, 112, 8174-8175.
Rosenbloom, et al., "Type 2 Diabetes mellitus in the child and adolescent", Pediatric Diabetes, 2008, p. 512-526.
Rosenstock, et al., "Efficacy and tolerability of initial combination therapy with vildagliptin and pioglitazone compared with component montherapy in patients with type 2 diabetes". Diabetes, Obesity and Metabolism, Mar. 2007, vol. 9, No. 2, p. 175-185.
Rosenstock, et al., Sitagliptin Study 019 Groups, Efficacy and safety of the dipeptidyl peptidase-4 inhibitor sitagliptin, Clinical Therapeutics, 2006, vol. 28, Issue 10, p. 1556-1568.
Rosenstock, J. et al., "Alogliptin added to insulin therapy in patients with type 2 diabetes reduces HbA1c without causing weight gain or increased hypoglycaemia". Diabetes, Obesity and Metabolishm, Dec. 2009, vol. 11. No. 12, p. 1145-1152.
Russell-Jones, D. et al., "Liraglutide vs insulin glargine and placebo in combination with metformin and sulfonylurea therapy in type 2 diabetes mellitus (LEAD-5 met+SU): a randomised controlled trial." Diabetologia, 2009, vol. 52, pp. 2046-2055.
Salomon, J., et al; Ultraviolet and g-Ray-Induced Reactions of Nucleic Acid Constituents. Reactions of Purines with Amines; Photochemistry and Photobiology (1974) vol. 19 pp. 21-27.
Sarafidis, P. et al., "Cardiometabolic Syndrome and Chronic Kidney Disease: What is the link?"JCMS 2006, 1: p. 58-65.
Sathananthan, A., et al., "Personalized pharmacotherapy for type 2 diabetes mellitus". Personalized Medicine 2009 Future Medicine Ltd, vol. 6, No. 4, Jul. 2009, p. 417-422.
Sauer, R, et al. "Water-soluble phosphate prodrugs of 1-Propargyl-7-styrylxanthine derivatives, A2A-selective adenosine receptor antagonists". Journal Med. Chem., vol. 43, Issue 3, Jan. 2000, p. 440-448.
Schmidt, D. et al., "Fibromatosis of Infancy and Childhood Histology, Ultrastructure and Clinicopathologic Correlation." Zeitschrift für Kinderchirurgie, 1985, vol. 40, No. 1, pp. 40-46.
Schwartz, M. S. et al., "Type 2 Diabetes Mellitus in Childhood: Obesity and Insulin Resistance". JAOA Review Article, vol. 108, No. 9, Sep. 2008, p. 518.
Scientific Discussion: "Eucreas. Scientific discussion". Online Oct. 2007, p. 1-27, URL:http://www.emea.europa.eu/humandocs/PDFs/EPAR/eucreas/H-807-en6.pdf. see point 2. quality aspects pp. 2-4. (EMEA).
Chisari, A. et al. "Sulphinyl, Sulphonyl, and Sulphonium Groups as Leaving Groups in Aromatic Nucleophilic Substitutions." Journal of the Chemical Society, Perkin Transactions II, 1982, pp. 957-959.
Clinical Trial NCT00622284 (published online at clinicaltrials.gov on Feb. 22, 2008).
Clinical Trials. "View of NCT00601250 on Jan. 25, 2008: Efficacy and Safety of BI 1356 vs Placebo added to Metformin Background Therapy in Patients with Type 2 Diabetes" Clinical Trials. Gov Archive, [Online] Jan. 25, 2008 URL:http://clinicaltrials.gov/archive/NCTO0601250/2008_01_25 [retrieved on Feb. 27, 2009].
Clinical Trials. NCT00622284. "Efficacy and safety of BI 1356 in combination with metformin in patients with type 2 diabetes" ClinicalTrials.gov (Online) No. NCT00622284, Feb. 13, 2008, p. 1-5, URL:http://clinicaltrial.gov/ct2/show/.
Clinical Trials. View of NCT00730275 updated on Aug. 7, 2008. "A study to assess the pharmacokinetics, safety and tolerability of Sitagliptin in adolescents". http://clinicaltrials.gov/archive/NCT00730275/2008_08_07.
Clinical Trials: NCT00954447, View on Jun. 14, 2010. "Efficacy and Safety of Linagliptin in Combination with Insulin in Patients with Type 2 Diabetes". <http://clinicaltrials.gov/archive/NCT00954447/2010_06_14>.
Clinical Trials: NCT00309608, "Efficacy and Safety of BI 1356 BS (Linagliptin) in Combination With Metformin in Patients With type2 Diabetes" Boehringer Ingelheim Pharmaceuticals, last updated: Dec. 11, 2013.
Clinical Trials: NCT00309608. Efficacy and safety of BI 1356 in combination with metformin in patients with type2 diabetes. Boehringer Ingelheim Pharmaceuticals, Jan. 27, 2009. Clinical Trials.gov . http://clinicaltrials.gov/archive/NCT00309608/2009_01_27.
Clinical Trials: NCT00602472. "BI 1356 in combination withe metformin and a sulphonylurea in Type 2 Diabetes". DrugLib.com, Nov. 3, 2008. http://www.druglib.com/trial/08/NCT00309608.html.
Clinical Trials: NCT00622284. Efficacy and Safety of BI 1356 in Combination with Metformin in Patients with Type 2 Diabetes. Boehringer Ingelheim Pharmaceuticals, Aug. 2008. http://clinicaltrials.gov/archive/ NCT00622284/2010_01_13.
Clinical Trials: NCT00798161. "Safety and efficacy of Bi 1356 Plus Metformin in Type 2 Diabetes, Factorial Design". Clinical Trials.gov archive. A Service of the U.S> National Institutes of Health. Nov. 24, 2008, p. 1-3. http://clinicaltrials.gov/archive/NCT00798161/2008_11_24.
Combs, D. W. et al., "Phosphoryl Chloride Induced Ring Contraction of 11,4-Benzodiazepinones to Chloromethylquinazolines". J. Heterocyclic Chemistry, BD. 23, 1986, p. 1263-1264.
Conarello, S.L. et al., "Mice lacking dipeptidyl peptidase IV are protected against obesity and insulin resistance". PNAS, May 27, 2003, vol. 100, No. 11, p. 6825-6830.
Conarello, S.L. et al; "Mice lacking dipeptidyl peptidase IV are protected against obesity and insulin resistance," PNAS 2003; 100:6825-6830; originally published online May 14, 2003; information current as of Dec. 2006. www.pnas.org/cgi/content/full/100/11/6825.
Cotton, M.L. et al., "L-649,923—The selection of an appropriate salt form and preparation of a stable oral formulation." International Journal of Pharmaceutics, 1994, vol. 109, Issue 3, pp. 237-249.
Cygankiewicz, Andrzej et al., Investigations into the Piperazine Derivatives of Dimethylxanthine:, Acta Polon. Pharm. [Papers of Polish Pharmacology], XXXOV, No. 5, pp. 607-612, 1977.
Dave, K.G. et al., "Reaction of Nitriles under Acidic Conditions, Part I. A General Method of Synthesis of Condensed Pyrimidines", J. Heterocyclic Chemistry, BD, 17, 1, ISSN 0022-152X,Nov. 1980, p. 1497-1500.
Dave, Rutesh H. "Overview of pharmaceutical excipients used in tablets and capsules." Drug Topics, Oct. 24, 2008.
Deacon, Carolyn F., et al., "Linagliptin, a xanthine based dipeptyl peptidase-4 inhibitor with an unusual profile for the treatment of type 2 diabetes" Expert Opinion Investig. Drugs 2010, 19 (1) p. 133-140.

(56) References Cited

OTHER PUBLICATIONS

Deacon, C.F. et al; "Dipeptidyl peptidase IV inhabitation as an approach to the treatment and prevention of type 2 diabetes: a historical perspective;" Biochemical and Biophysical Research Communications (BBRC) 294 (2002) 1-4.
Deacon, C.F., et al. Inhibitors of dipeptidyl peptidase IV: a novel approach for the prevention and treatment of Type 2 diabetes? Expert Opinion on Investigational Drugs, Sep. 2004, vol. 13, No. 9, p. 1091-1102.
Deacon, Carolyn F. et al. "Linaglipitn, a xanthine-based dipeptidyl peptidase-4 inhibitor with an unusual profile for the treatment of type 2 diabetes" Expert Opin. Investig. Drugs (2010) 19(1): 133-140.
Definition of "prevent", e-dictionary, Aug. 15, 2013, http://dictionary.reference.com/browse/prevent.
DeMeester, I. et al.; "CD26, let it cut or cut it down", Review: Immunology Today; Aug. 1999, vol. 20, No. 8 pp. 367-375.
Demuth, H-U. et al., "Type 2 diabetes—Therapy with dipeptidyl peptidase IV inhibitors". Biochimica et Biophysica Acta, vol. 1751(1), 2005, p. 33-44.
Diabetes Frontier, 2007, vol. 18, No. 2, p. 145-148.
Diabetes Health Center, "Diabetic Retinopathy—Prevention." Retrieved online Mar. 22, 2011. www.diabetes.webmd.com/tc/diabetic-retinopathy-prevention <http://www.diabetes.webmd.com/tc/diabetic-retinopathy-prevention?print=true>.
Diabetesincontrol.com "EASD: Eucreas, a Combination of Galvus and Metformin, Recommended for Approval." Diabetes in Control. com, Sep. 25, 2007, Retrieved from internet on Nov. 30, 2012, http://www.diabetesincontrol.com/articles/53-diabetes-news/5145.
Diabetic Neuropathy, Retrieved online Mar. 6, 2012. www.mayoclinic.com/health/diabetic-neuropathy/DS01045/METHOD=print&DSE <http://www.mayoclinic.com/health/diabetic-neuropathy/DS01045/METHOD=print&DSE>.
Drucker, et al.., The incretin system:glucagon-like peptide-1 receptor agonists and dipeptidyl peptidase-4 inhibitors in type 2 diabetes. Lancet, 2006, 368: 1696-705.
Dugi, K.A. et al., "BI 1356, a novel xanthine-based DPP-IV inhibitor, exhibits high potency with a wide therapeutic window and significantly reduces postprandial glucose excursions after an oGTT". Diabetologia, vol. 50, No. Suppl 1, Sep. 2007, p. S367, and 43rd Annual Meeting of the European Association for the Study of Diabetes; Amsterdam, Netherlands, Sep. 18-21, 2007.
Dunitz, J. et al.., "Disappearing Polymorphs." Acc. Chem. Res. 1995, vol. 28, No. 4, pp. 193-200.
Eckhardt Matthias et al: 8-(3-(R)-aminopiperidin-1-yl)-7-but-2-yny 1-3-methyl-1-(4-methyl-quina zolin-2-ylmethyl)-3,7-dihydropurine-2,6-dione (BI 1356), a highly potent, selective, long-acting, and orally bioavailable DPP-4 inhibitor for the treatment of type 2 diabetes: Journal of Medicinal Chemistry, American Chemical Society. Washington.; US, vol. 50, No. 26, Dec. 1, 2007, p. 6450-6453.
Eckhardt, M. et al., "3,5-dihydro-imidazo[4,5-d]pyridazin-4-ones: a class of potent DPP-4 inhibitors" Bioorganic & Medicinal Chemistry Letters, Pergamon, Elsevier Science, GB, vol. 18, No. 11, Jun. 1, 2008, pp. 3158-3162, XP022711188.
Edosada, C. Y. et al. "Selective Inhibition of Fibroblast Activation Protein Protease Based on Dipeptide Substrate Specificity." The Journal of Biological Chemistry, 2006, vol. 281, No. 11, pp. 7437-7444.
Elrishi M A et al: "The dipeptidyl-peptidase-4 (D::-4) inhibitors: A new class of oral therapy for patients with type 2 diabetes mellitus" Practical Diabetes International Chichester, vol. 24, No. 9, Nov. 1, 2007 pp. 474-482.
eMedicine Health, "Diabetes Causes." Retrieved from internet on Aug. 22, 2013. <http://www.onhealth.com/diabetes_health/page3.htm#diabetes_causes>.
Eucreas Scientific Discussion, 2007, p. 1-27, www.emea.europa.eu/humandocs/PD/Fs/EPAR/eucreas/H-807-en6.pdf, Anonymous.
Ferreira, L. et al., "Effects of Sitagliptin Treatment on Dysmetabolism, Inflammation, and Oxidative Stress in an Animal Model of Type 2 Diabetes (ZDF Rat)." Mediators of Inflammation, 2010, vol. 2010, pp. 1-11.

Ferry, Robert Jr., "Diabetes Causes." eMedicine Health, MedicineNet.com, 2013, Retrieved from Internet on Aug. 22, 2013, http://www.onhealth.com/diabetes_health/page3.htm#diabetes_causes.
Florez, J. et al. "TCF7L2 Polymorphisms and Progression to Diabetes in the Diabetes Prevention Program." The New England Journal of Medicine, 2006, vol. 355, No. 3, pp. 241-250.
Florez, Jose C., et al., "TCF7L2 Polymorphisms and progression to diabetes in the diabetes prevention program". New England Journal of Medicine, MA Medical Society, vol. 355, No. 2, Jul. 20, 2006, p. 241-250.
Forst, T. et al., "The Novel, Potent, and Selective DPP-4 Inhibitor BI 1356 Significantly Lowers HbA1c after only 4 weeks of Treatment in Patients with Type 2 Diabetes." Diabetes, Jun. 2007, Poster No. 0594P.
Fukushima et al., Drug for Treating Type II Diabetes (6), "action-mechanism of DPP-IV inhibitor and the availability thereof" Mebio, 2009, vol. 26, No. 8, p. 50-58.
Gallwitz, B. "Sitagliptin with Metformin: Profile of a Combination for the Treatment of Type 2 Diabetes". Drugs of Today, Oct. 2007, 43(10), p. 681-689.
Gallwitz, B. et al., "Saxagliptin, a dipeptidyl peptidase IV inhibitor for the treatment of type 2 diabetes". IDRUGS, vol. 11, No. 12, Dec. 2008, p. 906-917.
Gallwitz, B. et al., DPP IV inhibitors for the Treatment of Type 2 Diabetes; Diabetes Frontier (2007) vol. 18, No. 6 pp. 636-642.
Garber, A. J. et al., "Effects of Vildagliptin on Glucose Control in Patients with Type 2 Diabetes Inadequately Controlled with a Sulphonylurea". Diabetes, Obesity and Metabolism (2008) vol. 10 pp. 1047-1055.
Garber, A.J. et al., "Update: Vildaglitin for the treatment of Type 2 diabetes" Expert Opinion on Investigational Drugs, 200801GB, vol. 17, No. 1, Jan. 2008, p. 105-113.
Garcia-Soria, et al., "The dipeptidyl peptidase-4 inhibitor PHX1149 improves blood glucose control in patents with type 2 diabetes mellitus". Diabetes, Obesity and Metabolism, Apr. 2008, vol. 10, No. 4, p. 293-300.
Geka, 2001, vol. 67, No. 11, p. 1295-1299.
Gennaro, Alfonso R. Remington Farmacia, 2003, Spanish copy: p. 828, English copy: pp. 711-712, Preformulation, Chapter 38.
Gennaro, Alfonso R., Remington Farmacia, 19th Edition, Spanish copy, 1995, p. 2470.
Gennaro, Alfonso, R; Remington: The Science and Practice of Pharmacy: Oral Solid Dosage Forms; Mack Publishing Company, Philadelphia, PA (1995) vol. II, 19th Edition, Ch. 92 pp. 1615-1649.
Giron, D.; Thermal Analysis and Calorimetric Methods in the Characterisation of Polymorphs and Solvates; Thermochimica Acta (1995) vol. 248 pp. 1-59.
Glucotrol XL (glipizide), package insert, Pfizer, Apr. 1, 2002.
Goldstein, L.A., et al., "Molecular cloning of seprase: a serine integral membrane protease from human melanoma." Biochimica et Biophysica Acta, vol. 1361, 1997, No. 1, pp. 11-19.
Gomez-Perez, et al, "Insulin Therapy:current alternatives", Arch. Med.Res. 36: p. 258-272 (2005).
Graefe-Mody et al., "The novel DPP-4 inhibitor BI 1356 (proposed tradename ONDERO) and Metformin can be Safely Co-administered Without Dose Adjustment." Poster No. 553-P ADA Jun. 6-10, 2008, San Francisco http://professional.diabetes.org/content/posters/2008/p553-p.pdf. professional.diabetes.org/content/posters/2008/p553-p.pdf.
Graefe-Mody, et al; Evaluation of the Potential for Steady-State Pharmacokinetic and Phamacodynamic Interactions Between the DPP-4 Inhibitor Linagliptin and Metformin in Healthy Subjects; Currents Medical Research and Opinion (2009) vol. 25, No. 8 pp. 1963-1972.
Graefe-Mody, U. et al., "Effect of Renal Impairment on the Pharmacokinetics of the Dipeptidyl Peptidase-4 Inhibitor Linagliptin." Diabetes, Obseity and Metabolism, 2011, pp. 939-946.
Greene, T.W, et al., "Protection for the Amino Group". Protective Groups in Organic Synthesis, 3rd edition, 1999, p. 494-653.
Groop, P.-H. et al., "Effects of the DPP-4 Inhibitor Linagliptin on Albuminuria in Patients with Type 2 Diabetes and Diabetic Nephropathy." 48th EASD Annual Meeting, Berlin, Abstract 36, Oct.

(56) References Cited

OTHER PUBLICATIONS

2012. <http://www.abstractsonline.com/Plan/ViewAbstract.aspx?sKey=0b0017b9-9e90-4695-b9af-b6870e96a921&cKey=421edb9c-b940-40f0-b282-8e61245561d5&mKey=2dbfcaf7-1539-42d5-8dda-0a94abb089e8>.

Gwaltney, S. "Medicinal Chemistry Approaches to the Inhibition of Dipeptidyl Peptidase IV", Current Topics in Medicinal Chemistry, 2008, 8, p. 1545-1552.

Halimi, et al. "Combination treatment in the management of type 2 diabetes focus on vildagliptin and metformin as a single tablet", Vascualr Health and Risk Management, 2008, 4(3) p. 481-92.

Haluzik, M. et al., "Renal Effects of DPP-4 Inhibitors: A Focus on Microalbuminuria." International Journal of Endocrinology, 2013, vol. 35, No. 6, pp. 1-7.

Hansen, H. et al., "Co-Administration of the DPP-4 Inhibitor Linagliptin and Native GLP-1 Induce Body Weight Loss and Appetite Suppression." 73rd Annual Meeting Science Session, ADA, Chicago, Jun. 21, 2013.

Hashida, Mitsuru, "Strategies for designing and developing oral administration formulations." Yakuji-Jiho, Inc., 1995, pp. 50-51.

Hayashi, Michio., "Recipe for Oral Hypoglycemic Agents to Pathological Condition" Pharmacy (2006) vol. 57, No. 9 pp. 2735-2739.

He, Y. L. et al., "Bioequivalence of Vildagliptin/Metformin Combination Tablets and Coadministration of Vildagliptin and Metformin as Free Combination in Healthy Subjects". J. Clinical Pharmacology, 2007, vol. 47, No. 9, Abstracts of the 36th Annual Meeting of the American College of Clinical Pharmacology, San Francisco, CA, Abstract 116, p. 1210.

He, Y.L. et al., "The influence of hepatic impariment on the pharmacokinetics f the dipeptidyl peptidase IV (DPP-4) inhibitor vildagliptin" European Journal of Clinical Pharmacology, vol. 63, No. 7, May 8, 2007, p. 677-686.

Headland, K. et al., "The Effect of Combination Linagliptin and Voglibose on Glucose Control and Body Weight." 73rd Annual Meeting Science Session, ADA, Chicago, Jun. 21, 2013.

Heihachiro, A. et al., "Synthesis of Prolyl Endopeptidase Inhibitors and Evaluation of Their Structure-Activity Relationships: In Vitro Inhibition of Prolyl Endopeptidase from Canine Brain." 1993, Chemical and Pharmaceutical Bulletin, vol. 41, pp. 1583-1588.

Heise, T. et al., "Treatment with BI 1356, a Novel and Potent DPP-IV Inhibitor, Significantly Reduces Glucose Excursions after an oGTT in Patients with Type 2 Diabetes." A Journal of the American Diabetes Association, Jun. 2007, vol. 56, Supplement 1, Poster No. 0588P.

Herman, G. A. et al., "Dipeptidyl Peptidase-4 Inhibitors for the Treatment of Type 2 Diabetes: Focus on Sitagliptin." Clinical Pharmacology and Therapeutics, 2007, vol. 81, No. 5, pp. 761-767.

Herman, Gary et al. "Co-Administration of MK-0431 and Metformin in Patients with Type 2 Diabetes Does Not Alter the Pharmacokinetics of MK-0431 or Metformin" (2005) Journal of American Diabetes Association vol. 54, Supplement 1, 3 pgs.

Hermann, Robert, et al; Lack of Association of PAX4 Gene with Type 1 Diabetes in the Hungarian Populations; Diabetes (2005) vol. 54 pp. 2816-2819.

Hermansen, K., "Efficacy and Safety of the Dipeptidyl Peptidase-4 Inhibitor, Sitagliptin, in Patients with Type 2 Diabetes Mellitus Inadequately Controlled on Glimepiride Alone or on Glimepiride and Metformin". Diabetes, Obesity and Metabolism (2007) vol. 9, No. 5 pp. 733-745.

Hilfiker, R. et al., "Relevance of Solid-state Properties for Pharmaceutical Products." Polymorphism in the Pharmaceutical Industry, 2006, Chapter 1, pp. 1-19.

Hocher, B. et al., "Renal and Cardiac Effects of DPP-4 Inhibitors—from Preclinical Development to Clinical Research." Kidney & Blood Pressue Research, 2012, vol. 36, No. 1, pp. 65-84.

Holman, et al., "Addition of biphasic, prandial, or basal insulin to oral therapy in type 2 diabetes", N. England Journal Medicine, p. 1716-1730, 2007.

Horsford, E. N. "On the source of free hydrochloric acid in the gastric juice." Proceedings of the Royal Society of London, Published in 1868-1869, vol. 17, pp. 391-395.

Hu, Y. et al., "Synthesis and Structure-activity Relationship of N-alkyl Gly-boro-Pro Inhibitors of DPP4, FAP, and DPP7." Bioorganic & Medicinal Chemistry Letters 15, 2005, pp. 4239-4242.

Huettner Silks et al: "BI 1356, a novel and selective xanthine based DPP-IV inhibitor, demonstrates good safety and tolerability with a wide therapeutic window" Diabetes< American Diabetes Association, US, vol. 56, No. Suppl 1, Jun. 1, 2007, p. A156.

Hunziker, D. et al, "Inhibitors of DPP IV-recent advances and structural views", Current Topics in Medicinal Chemistry, 2005, vol. 5 issue 16, pp. 1623-1637.

Huttner, S. et al., "Safety, Tolerability, Pharmacokinetics, and Pharmacodynamics of Single Oral Doses of BI 1356, an Inhibitor of Dipeptidyl Peptidase 4, in Healthy Male Volunteers." Journal of Clinical Pharmacology, 2008, vol. 48, No. 10, pp. 1171-1178.

International Search Report and Written Opinion for PCT/EP2007/054201 mailed Aug. 29, 2007.

Inukai, T., "Treatment of Diabetes in Patients for Whom Metformin Treatment is Not Appropriate." Modern Physician, 2008, vol. 28, No. 2, pp. 163-165.

Januvia; Patient Information; 2010.

Johansen, O. E. et al., "Cardiovascular safety with linagliptin in patients with type 2 diabetes mellitus: a pre-specified, prospective, and adjudicated meta-analysis of a phase 3 programme." Cardiovascular Diabetology, Biomed Central, 2012, vol. 11, No. 1, pp. 1-10.

Johansen, O.E. et al., "b-cell Function in Latnet Autoimmune Diabetes in Adults (LADA) Treated with Linagliptin Versus Glimepiride: Exploratory Results from a Two Year Double-Blind, Randomized, Controlled Study." www.abstractsonline.com, Jun. 10, 2012, XP-002708003.

John Hopkins Children's Center, "Liver Disorders and Diseases." Retrieved online May 26, 2014 <http://www.hopkinschildrens.org/non-alcoholic-fatty-liver-disease.aspx>.

Jones, R.M. et al., "GPR119 agonists for the treatment of type 2 diabetes". Expert Opinion on Therapeutic Patents 2009 Informa Healthcare for GBR LNKSD—DOI: 10.1517/13543770903153878, vol. 19, No. 10, Oct. 2009, p. 1339-1359.

Kanada, S. et al., "Safety, tolerability, pharmacokenetics and pharmacodynamics of multiple doses of BI 1356 (proposed tradename ONDERO), a dipeptidyl peptidase 4 inhibitor, in Japanese patients with type 2 diabetes" Diabetes, vol. 57, No. Suppl. 1, Jun. 2008, p. A158-A159 and 68th Annual Meeting of the American Diabetes Association: San Francisco, CA, Jun. 6-10, 2008.

Kelly. T., "Fibroblast activation protein-cx and dipeptidyl peptidase IV (CD26)P: Cell-surface proteases that activate cell signaling and are potential targets for cancern therapy". Drug Resistence Update 8, 2005, vol. 8. No. 1-2, pp. 51-58.

Kharkevich, D. A., "Educational Literature" Pharmacology (1987) Third Edition, Meditsina Press, Moscow pp. 47-48.

Kibbe, A., Editor. Handbook of Pharmaceutical Excipients, Third Edition, Copovidon-pp. 196-197, Date of Revision: Dec. 16, 2008. Mannitol-pp. 424-425, Date of Revision: Feb. 19, 2009, Published in 2009.

Kidney Disease (Nephropathy), Retrieved online May 13, 2013. www.diabetes.org/living-with-diabetes/complications/kidney-disease-nephropathy.html <http://www.diabetes.org/living-with-diabetes/complications/kidney-disease-nephropathy.html>.

Kim, D. et al., "(2R)-4-Oxo-4-(3-(Trifluoremethyl)-5,6-dihydro[1,2,4]triazolo[4,3-a]pyrazin-7(8H)-yl]-1-(2,4,5-trifluorophenyl)butan-2-amine: A Potent, Orally Active Dipeptidyl Peptidase IV inhibitor for the Treatment of Type 2 Diabetes." Journal Med. Chem, 2005, 48, p. 141-151.

Kim, Kwang-Rok et al., "KR-62436, 6-{2-{2-(5-cyano4,5-dihydropyrazol-1-yl)-2-oxoethylamino}ethylamino}nicotinonitrile, is a novel dipeptidyl peptidase-IV (DDP-IV) inhibitor with anti-hyperglycemic activity" European Journal of Pharmacology 518, 2005, p. 63-70.

Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.

Shanks, N. et al., Are animal models predictive for humans?, PEHM, Philosophy, Ethics, and Humanaities in Medicine, 4(2), 2009, 1-20.

Sharkovska, Y., et al., "DPP-4 Inhibition with Linagliptin Delays the Progression of Diabetic Nephropathy in db/db Mice." 48th EASD

(56) References Cited

OTHER PUBLICATIONS

Annual Meeting, Berlin, Abstract 35, Oct. 2012. <http://www.abstractsonline.com/Plan/ViewAbstract.aspx?sKey=0b0017b9-9e90-4695-b9af-b6870e96a921&cKey=8eff47ae-db49-4c36-a142-848ac068c405&mKey=2dbfcaf7-1539-42d5-8dda-0a94abb089e8>.
Shintani, Maki, et al., "Insulin Resistance and Genes" Circulatory Sciences (1997) vol. 17, No. 12 pp. 1186-1188.
Silverman, G. et al., "Handbook of Grignard Reagents." 1996, Retrieved online: <http://books.google.com/books?id=82CaxfY-uNkC&printsec=frontcover&dq=intitle:Handbook+intitle:of+intitle:Grignard+intitle:Reagents&hl=en&sa=X&ei=g06GU5SdOKngsATphYCgCg&ved=0CDYQ6AEwAA#v=onepage&q&f=false>.
Singhal, D. et al., "Drug polymorphism and dosage form design: A practical perspective." Advanced Drug Delivery Reviews, 2004, vol. 56, pp. 335-347.
Sortino, M.A. et al., "Linagliptin: a thorough characterization beyond its clinical efficacy." Frontiers in Endocrinology, 2013, vol. 4, Article 16, pp. 1-9.
St. John Providence Health Center, "Preventing Obesity in Children and Teens." Retrieved from internet on Aug. 22, 2013, http://www.stjohnprovidence.org/Health I nfoLib/swarticle.aspx?type=85&id=P07863.
Stahl, P.H., "Handbook of Pharmaceutical Salts". C.G. Wermuth, Wiley-VCH, 2002, p. 61.
Sune Negre, J. M. "New Galenic Contributions to Administration Forms". Continued Training for Hospital Pharmacists 3.2., (Publication date unavailable), Retrieved from internet on Feb. 23, 2011, http://www.ub.es/legmh/capitols/sunyenegre.pdf.
Tamm, E, et al., "Double-blind study comparing the immunogenicity of a licensed DTwPHib-CRM197 conjugate vaccine (Quattvaxem TM) with three investigational, liquid formulations using lower doses of Hib-CRM197 conjugate". Science Direct, Vaccine, Feb. 2005, vol. 23, No. 14, p. 1715-1719.
Tanaka, S.. et al; "Suppression of Arthritis by the Inhibitors of Dipeptidyl Peptidase IV," In. J. Immunopharmac., vol. 19, No. 1, pp. 15-24, 1997.
Targher, G. et al., "Prevalence of Nonalcoholic Fatty Liver Disease and Its Association With Cardiovascular Disease Among Type 2 Diabetic Patients." Diabetes Care, 2007, vol. 30, No. 5, pp. 1212-1218.
Third Party Observation for application No. EP20070728655, May 13, 2013.
Thomas, L, et al: "BI 1356, a novel and selective xanthine beased DPP-IV inhibitor, exhibits a superior profile when compared to sitagliptin and vildagliptin." Diabetologoa, vol. 50, No. Suppl. 1, Sep. 2007, p. S363.
Thomas, L., "Chronic treatment with the Dipeptidyl Peptidase-4 Inhibitor BI 1356[9R)-8-(3-Amino-piperidin-1-yl)-7-but-2-yny1-3-methy1-1(4-methyl-quinazolin-2-ylmethyl)-3,7-dihydro-purine-2,6-dione] Increases Basal Glucagon-Like Peptide-1 and Improves Glycemic Control in Diabetic Rodent Models" The Journal of Pharmacology and Experimental Therapeutics, Feb. 2009, vol. 328, No. 2, pp. 556-563.
Thomas, Leo et al: "(R)-8-(3-Amino-piperidin-1-y1)-7-but-2-ynyl-3-methyl-1- (4-methyl-quinazolin-2-ylmethyl)-3,7-dihydro-purine-2,6-dione (BI 1356), a Novel Xanthine-Based Dipeptidyl Peptidase 4 Inhibitor, Has a Superior Potency and Longer Duration of Action Compared with Other Dipeptidyl Peptidase-4 Inhibitors." Journal of Pharmacology and Experimental Therapeutics, 2008, vol. 325, No. 1, pp. 175-182.
Thornber, C.W., "Isosterism and Molecular Modification in Drug Design." Chemical Society Reviews, 1979, pp. 563-580.
Tounyoubyou, "Symposium-19: Future Perspectives on Incretion Therapy in Diabetes." 2008, vol. 51, Suppl. 1, p. S-71, S19-2.
Tradjenta, Highlights of Prescribing Information (revised Sep. 2012).
Tribulova, N. et al. "Chronic Disturbances in NO Production Results in Histochemical and Subcellular Alterations of the Rat Heart." Physiol. Res., 2000, vol. 49, No. 1, pp. 77-88.
Tsujihata, et al., "TAK-875, an orally available G protein-Coupled receptor 40/Free fatty acid receptor 1 Agonist, Enhances Glucose Dependent Insulin Secretion and improves both Postprandial and Fasting hyperglycemic in type 2 Diabetic rats", J. Pharm Exp. 2011, vol. 339, No. 1, p. 228-237.
Tsuprykov, O. et al., Linagliptin is as Efficacious as Telmisartan in Preventing Renal Disease Progression in Rats with 5/6 Nephrectomy, 73rd Annual Meeting Science Session, ADA, Chicago, Jun. 2013. <http://www.abstractsonline.com/Plan/ViewAbstract.aspx?sKey=e68ac573-fe45-4c2f-9485-6270854fc10b&cKey=3c387569-04de-4f8c-b025-b358df91ca64&mKey=%7b89918D6D-3018-4EA9-9D4F-711F98A7AE5D%7d>.
U.S. Appl. No. 12/724,653, filed Mar. 16, 2010—Xanthine Derivatives, the Preparation Thereof and Their Use as Pharmaceutical Compositions. Inventor: Frank Himmelsbach, et al.
U.S. Appl. No. 12/767,855, filed Apr. 27, 2010—Xanthine Derivatives, the Preparation Thereof and Their use as Pharmaceutical Compositions. Inventor: Frank Himmelsbach, et al.
Uhlig-Laske, B. et al., "Linagliptin, a Potent and Selective DPP-4 Inhibitior, is Safe and Efficacious in Patients with Inadequately Controlled Type 2 Diabetes Despite Metformin Therapy". 535-P Clinical Therapeutics/New Technology—Pharmacologic Treatment of Diabetes or Its Complications, Posters, vol. 58, Jun. 5, 2009, p. A143.
United Healthcare, "Diabetes." Retrieved from internet on Aug. 22, 2013, http://www.uhc.com/source4women/health_topics/diabetesirelatedinformation/dOf0417b073bf11OVgnVCM1000002f1Ob10a_htm.
Villhauer, E.B., "1[[3-Hydroxy-1-adamantyl)amino]acetyl]-1-cyano-(S)-pyrrolidine: A Potent, Selective, and Orally Bioavailable Dipeptidyl Peptidase IV Inhibitor with Antihyperglycemic Properties" Journal Med. Chem, 2003, 46, p. 2774-2789.
Villhauer, E.B., et al., "1-{2-{5-Cyanopyridin-2-yl)amino}-ethylamino}acetyl-1-1(S)-pyrrolidine-carbonitrile: A Potent, Selective, and Orally Bioavailable Dipeptidyl Peptidase IV Inhibitor with Antihyperglycemic Properties". Journal of Medical Chemistry, 2002, vol. 45, No. 12, p. 2362-2365.
Wang Y et al: "BI-1356. Dipeptidyl-peptidase IV inhibitor, antidiabetic agent" Drugs of the Future, Prous Science, ES, vol. 33, No. 6, Jun. 1, 2008, pp. 473-477.
Wertheimer, et al., "Drug Delivery Systems improve pharmaceutical profile and faciliate medication adherence", Adv. Therapy 22: p. 559-577 (2005).
White, John R. Jr., "Dipeptidyl Peptidase-IV Inhibitors: Phamacological Profile and Clinical Use". Clinical Diabetes, Apr. 2008, vol. 26, No. 2, pp. 53-57.
Wikipedia, Annulation. Jun. 23, 2008, http://en.wikipedia.org/wiki/Annelation.
Williams-Herman, D. et al., "Efficacy and safety of initial combination therapy with sitagliptin and metformin in patients with type 2 diabetes: a 54-week study". Current Medical Research and Opinion, Informa Healthcare, GB, vol. 25, No. 3, Jan. 2009, p. 569-583.
Wolff, M.E.: "Burger's Medicinal Chemistry and Drug Discovery" Fifth Edition, vol. 1: Principles and Practice, pp. 975-977, 1994, John Wiley & Sons, Inc.
World Health Organization (WHO). "Addendum 1 to "The use of stems in the selection of International Nonproprietary names (INN) for pharmaceutical substances"" Online Jun. 19, 2007, pp. 1-3, retrieved from URL: http://www.who.int/medicindedocs/index/assoc/s1414e/s1414e.pdf.
X-Ray Diffraction. The United States Pharmacopeia, 2002, USP 25 NF20, p. 2088-2089.
Yasuda, et al. "E3024 3-but-2-ynyl-5-methyl-2-piperazin-1-y1-3,5-dihydro-4H-imidazol [ 4,5-d]pyridazin-4-one tosylate, is a move, selective and competitive dipeptidyl peptidase-IV inhibitor". European Journal of Pharmacology, vol. 548, No. 1-3, Oct. 24, 2006, p. 181-187. Abstract.
Yoshikawa, Seiji et al.: Chemical Abstract of Japanese Patent No. WO 2003/104229 Preparation of purinone derivatives as dipeptidylpeptidase IV (DPP-IV) inhibitors, 2003.

(56) References Cited

OTHER PUBLICATIONS

Youssef, S. et al., "Purines XIV. Reactivity of 8-Promo-3,9-dimethylxanthine Towards Some Nucleophilic Reagents." Journal of Heterocyclic Chemistry, 1998, vol. 35, pp. 949-954.
Zejc, Alfred, et al; "Badania Nad Piperazynowymi Pochodnymi Dwumetyloksantyn" Acta Polon Pharm, XXXV (1976) Nr. 4 pp. 417-421.
Zhong, Qing et al; "Glucose-dependent insulinotropic peptide stimulates proliferation and TGF-? release from MG-63 cells," Peptides 24 (2003) 611-616.
Zhu, G. et al., "Stabilization of Proteins Encapsulated in Cylindrical Poly(lactide-co-glycolide) Implants: Mechanism of Stabilization by Basic Additives." Pharmaceutical Research, 2000, vol. 17, No. 3, pp. 351-357.
Zimmer et al; Synthesis of 8-Substituted Xanthines and their Oxidative Skeleton Rearrangement to 1-Oxo-2,4,7,9-tetraazaspiro[4,5]dec-2-ene-6,8,10-triones; Euripean Journal Organic Chemistry (1999) vol. 9 pp. 2419-2428.
Abstract in English for German DE10109021, 2002.
Abstract in English for German DE2205815, 1972.
Abstract in English for German EP0023032, 1981.
Abstract in English for JP 2002/348279, Dec. 4, 2002.
Abstract in English for JP 2003/286287, Oct. 10, 2003.
Abstract in English, for KR20070111099, Nov. 11, 2007.
Adebowale, K.O. et al., "Modification and properties of African yam bean (Sphenostylis stenocarpa Hochst. Ex A. Rich.) Harms starch I: Heat moisture treatments and annealing." Food Hydrocolloids, 2009, vol. 23, No. 7, pp. 1947-1957.
Ahren, BO, et al; Improved Meal-Related b-Cell Function and Insulin Sensitivity by the Dipeptidyl Peptidase-IV Inhibitor Vildagliptin in Metformin-Treated Patients with Type 2 Diabetes Over 1 Year; Diabetes Care (2005) vol. 28, No. 8 pp. 1936-1940.
Ahren, BO; "DPP-4 inhibitors", Best practice and research in clinical endocrinology and metabolism—New therapies for diabetes 200712 GB LNKD- DOI:10.1016/J. Beem.2007.07.005, vol. 21, No. 4, Dec. 2007, pp. 517-533.
Al-Masri, I.M. et al., "Inhibition of dipeptidyl peptidase IV (DPP IV) is one of the mechanisms explaining the hypoglycemic effect of berberine." Journal of Enzyme Inhibition and Medicinal Chemistry, 2009, vol. 24, No. 5, pp. 1061-1066.
Al-Masri, Journal of Enzyme Inhibition and Medicinal Chemistry, "Inhibition of dipeptyl peptidase IV (DPP iv) is one of the mechanisms explaining hypoglycemic effect of berberine", 2009.
Alter, M. et al. "DPP-4 Inhibition on Top of Angiotensin Receptor Bockade Offers a New Therapeutic Approach for Diabetic Nephropathy." Kidney and Blood Pressue Research, 2012, vol. 36, No. 1, pp. 119-130.
American Diabetes Association, "Standards of Medical Care in Diabetes—2008." Diabetes Care, Jan. 2008, vol. 31, Supplement 1, pp. S12-S54.
Anonymous, Clinicaltrials.gov, 2008, No. NCT00622284, "Efficacy and Safety of BI 1356 in combination with metformin in patients with type 2 diabetes" p. 1-5.
Anstee, Quentin M. et al. "Mouse models in non-alcholic fatty liver disease and steatohepatitis research" (2006) International Journal of Expermental Pathology, vol. 87, pp. 1-16.
Augeri, D.J. "Discovery and Preclinical Profile of Saxagliptin (GMB-477118): A Highly Potent, Long-Acting, Orally Active Dipeptidyl Peptidase IV Inhibitor for the Treatment of Type 2 Diabetes". Journal Med. Chem, 2005, vol. 48, No. 15, p. 5025-5037.
Augusti, D.V. et al., "Quantitative determination of the enantiomeric composition of thalidomide solutions by electrospray ionizatio tandem mass spectrometry". Chem Comm, 2002, p. 2242-2243.
Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.
Aulinger, B.A. et al., "Ex-4 and the DPP-IV Inhibitor Vildagliptin have Additive Effects to Suppress Food Intake in Rodents". Abstract No. 1545-P, 2008.

Balaban, Y.H. et al., "Dipeptidyl peptidase IV (DDP IV) in NASH patients" Annals of Hepatology, vol. 6, No. 4, Oct. 1, 2007, pp. 242-250, abstract.
Balbach, S. et al., "Pharmaceutical evaluation of early development candidates the 100 mg-approach." International Journal of Pharmaceutics, 2004, vol. 275, pp. 1-12.
Balkan, B. et al, "Inhibition of dipeptidyl peptidase IV with NVP-DPP728 increases plasma GLP-1 (7-36 amide) concentrations and improves oral glucose tolerance in obses Zucker rates". Diabetologia, 1999, 42, p. 1324-1331.
Bastin, R.J. et al., "Salt Selection and Optimization Procedures for Pharmaceutical New Chemical Entities". Organic Process Research and Development, 2000, vol. 4, p. 427-435.
Beljean-Leymarie et al., Hydrazines et hydrazones hétérocycliques. IV. Synthèses de dérivés de l'hydrazine dans la série des imidazo[4,5-d]pyridazinones-4, Can. J. Chem., vol. 61, No. 11, 1983, pp. 2563-2566.
Berge, S. et al., "Pharmaceutical Salts." Journal of Pharmaceutical Sciences, 1977, vol. 66, No. 1, pp. 1-19.
Bernstein, Joel "Polymorphism in Molecular Crystals." Oxford University Press, 2002, p. 9.
Bollag, R.J. et al; "Osteoblast-Derived Cells Express Functional Glucose-Dependent Insulinotropic Peptide Receptors," Endocrinology, vol. 141, No. 3, 2000, pp. 1228-1235.
Borloo, M. et al. "Dipeptidyl Peptidase IV: Development, Design, Synthesis and Biological Evaluation of Inhibitors." 1994, Universitaire Instelling Antwerpen, vol. 56, pp. 57-88.
Bosi, E. et al., "Effects of Vildagliptin on Glucose Control Over 24 Weeks in Patients With Type 2 Diabetes Inadequately Controlled With Metformin." Diabetes Care, 2007, vol. 30, No. 4, pp. 890-895.
Boulton, D.W. et al., "Safety, Tolerability, Pharmacokinetics and Pharmacodynamics of Once-Daily Oral Doses of Saxagliptin for 2 Weeks in Type 2 Diabetic and Healthy Subjects." Diabetes, 2007, Supplement 1, vol. 56, pp. A161.
Brazg, R. et al: "Effect of adding sitagliptin, a dipeptidyll peptidase-4 inhibitor, to metformin on 24-h glycaemic control and beta-cell function in patients with type 2 diabetes." Diabetes, Obesity and Metabolism, Mar. 2007, vol. 9, No. 2, Mar. 2007 pp. 186-193.
Brazg, Ronald, et al; Effect of Adding MK-0431 to On-Going Metforming Therapy in Type 2 Diabetic Patients Who Have Inadequate Glycemic Control on Metformin; Diabetes ADA (2005) vol. 54, Suppl. 1 p. A3.
Brittain, H.G., "Methods for the Characterization of Polymorphs: X-Ray Powder Diffraction," Polymorphism in Pharmaceutical Solids, 1999, p. 235-238.
Bundgaard, H. "Design of prodrugs: Bioreversible derivatives for various functional groups and chemical entities". Royal Danish School of Pharmacy, 1985, p. 1-92.
Busso et al., "Circulating CD26 is Negatively Associated with Inflammation in Human and Experimental Arthritis," Am. J. Path., vol. 166, No. 2, Feb. 2005, pp. 433-442.
Byrn, Stephen R. "Solid-State Chemistry of Drugs." Academic Press, 1982, pp. 1-27.
Caira, M.R., "Crystalline polymorphism of organic compounds" Topics in Current Chemistry, Springer, Berlin, vol. 198, 1998, p. 163-208.
Campbell, R. Keith "Rationale for Dipeptidyl Peptidase 4 Inhibitors: A New Class of Oral Agents for the Treatment of Type 2 Diabetes Mellitus." The Annals of Pharmacotherapy, Jan. 2007, vol. 41, pp. 51-60.
Chan, J.C. et al., "Safety and efficacy of sitagliptin in patients with type 2 diabetes and chronic renal insufficiency." 2008, Diabetes, Obesity and Metabolism, vol. 10, pp. 545-555.
Charbonnel, B. et al., "Efficacy and Safety of the Dipeptidyl Peptidase-4 Inhibitor Sitagliptin Added to Ongoing Metformin Therapy in Patients With Type 2 Diabetes Inadequately Controlled With Metformin Alone." Diabetes Care, 2006, vol. 29, No. 12, pp. 2638-2643.
Chaykovska, L. et al., "Effects of DPP-4 Inhibitors on the Heart in a Rat Model of Uremic Cardiomyopathy." www.plosone.org, 2011, vol. 6, No. 11, p. e27861.
ChemGaroo, "Leaving Group." 1999, Retrieved online: http://www.chemgapedia.de/vsengine/vlu/vsc/en/ch/12/oc/vluorganik/substitu-

(56) References Cited

OTHER PUBLICATIONS tion/sn_2/sn 2. vlu/Page/vsc/en/ch/12/oc/substitution/sn_2/abgangsgrupen/abgangsgruppe.vscml.html.
Chemical Abstract. EP412358, 1991:185517, Findeisen.
Chemical Abstract: FR2707641, 1995:543545, Dodey.
Chemical Abstract: No. 211513-37-0—Dalcetrapib. "Propanethioic acid, 2-methyl-,S-(2-[[[1-(2-ethylbutyl)cyclohexyl}carbonyl}amino}pheyl}ester". Formula: C23 H35 N 02 S. American Chemical Society. Sep. 20, 1998.
Chemical Abstract: No. 875446-37-0—Anacetrapib. "2-Oxazolidinone, 5-[3,5-bis(trifluoromethyl)phenyl]-3[[4'fluoro-2'methoxy-5'-(1-methylethyl)-4-(trifluoromethyl)[1,1'-biphenyl]-2-yl]methyl]-4-methyl-,(4S,5R)-" Formula: C30 H25 F10 N O3. American Chemical Society, Feb. 28, 2006.
Chemical Abstracts Accession No. 106:95577 Romanenko et al., "Synthesis and Biological Activity of 3-Methyl, 7- or 8-alkyl-7,8dialkyl, heterocyclic, and cyclohexylaminoxanthines," Zaporozh. Med. Institute (1986).
Chemical Abstracts Accession No. 1987:95577: Abstract of Romanenko et al., "Synthesis and biological activity of 3-methyl, 7- or 8-alkyl, 7,8-dialkyl, heterocyclic, and cyclohexylaminoxanthines," Zapoeozh, USSR, Farmatsevtichnii Zhurnal, 1986, (Kiev), vol. 5, 1986, pp. 41-44.
Chemical Abstracts Service, Database Accession No. Number RN 668270-12-01, 2004, "1H-Purine-2,6-dione, 8-[(3R)-3-amino-1-piperidinyl]-7-(2-butyn-1-yl)-3,7-dihydro-3-methyl-1-[(4-methyl-2-quinazolinyl)methyl]".
Chemistry Review: Tradjenta, "NDA 201280, CMC Director Review Tradjenta (Linagliptin) Tablets." Center for Drug Evaluation and Research, Aug. 9, 2010, Retrieved from the internet on Nov. 1, 2013, htip://www.accessdata.fda.gov/drugsatfda_docs/nda/2011/201280Orig1s000ChemR.pdf.
Baetta, R. et al., "Pharmacology of Dipeptidyl Peptidase-4 Inhibitors." Drugs, 2011, vol. 71, No. 11, pp. 1441-1467.
Blech, et al, Drug Metabolism and Deposition, "The Metabolism and Disposition of the Oral Dipeptidyl Peptidase-4 Inhibitor, Linagliptin, in Humans", 2009, vol. 38, No. 4, p. 667-678.
Cheon, et al., Biochemical Pharmacology, "Inhibition of dipeptidyl IV by novel inhibitors with pyrazolidine scaffold", 2005, vol. 70, p. 22-29.
Crowe, E. et al., "Early identification and management of chronic kidney disease: summary of NICE guidance." British Medical Journal, 2008, vol. 337, pp. 812-815.
Forst, T. et al., "The oral DPP-4 inhibitor linagliptin significantly lowers HbA1c after 4 weeks of treatment in patients with type 2 diabetes mellitus." Diabetes, Obesity and Metabolism, 2011, vol. 13, pp. 542-550.
Gallwitz, B. et al., "2-year efficacy and safety of linagliptin compared with glimepiride in patients with type 2 diabetes inadequately controlled on metformin: a randomised, double-blind, non-inferiority trial." Lancet, 2012, vol. 380, pp. 475-483.
Greischel, et al., Drug Metabolism and Deposition, "The Dipeptidyl Peptidase-4 Inhibitor Linagliptin Exhibits Time- and Dpse-Dependent Localization in Kidney, Liver, and Intestine after Intravenous Dosing: Results from High Resolution Autoradiography in Rats", 2010, vol. 38, No. 9, p. 1443-1448.
Guglielmi, C. et al., "Latent autoimmune diabetes in the adults (LADA) in Asia: from pathogenesis and epidemiology to therapy." Diabetes/Metabolism Research and Reviews, 2012, vol. 28, Supplement 2, pp. 40-46.
Heise, et al., Diabetes, Obesity and Metabolism, "Pharmacokinetics, pharmacokinetics and tolerability of mutilple oral doses of linagliptin, a dipeptidyl peptidase-4 inhibitor in male type 2 diabetes patients", 2009, vol. 11, No. 8, p. 786-794.
Hocher, B. et al., "The novel DPP-4 inhibitors linagliptin and BI 14361 reduce infarct size after myocardial ischemia/reperfusion in rats." International Journal of Cardiology, 2013, vol. 167, pp. 87-93.
Hull, R. et al., "Nephrotic syndrome in adults." British Medical Journal, 2008, vol. 336, pp. 1185-1190.
Isomaa, B. et al., "Cardiovascular Morbidity and Mortality Associated With the Metabolic Syndrome." Diabetes Care, 2001, vol. 24, No. 4, pp. 683-689.
Kendall, D. M. et al., "Incretin Mimetics and Dipeptidyl Peptidase-IV Inhibitors: A Review of Emerging Therapies for Type 2 Diabetes." Diabetes Technology & Therapeutics, 2006, vol. 8, No. 3, pp. 385-398.
Klein, T. et al., "Linagliptin alleviates hepatic steatosis and inflammation in a mouse model of non-alcoholic steatohepatitis." Medical Molecular Morphology, 2014, vol. 47, pp. 137-149.
Lakatos, P. L. et al "Elevated serum dipeptidyl peptidase IV (CD26, EC 3.4.14.5) activity in patients with primary biliary cirrhosis." Journal of Hepatol, 1999, vol. 30, p. 740.
Lyssenko, V. et al., "Mechanisms by which common variants in the TCF7L2 gene increase risk of type 2 diabetes." the Journal of Clinical Investigation, 2007, vol. 117, No. 8, pp. 2155-2163.
McNay, David E.G. et al., "High fat diet causes rebound weight gain." Molecular Metabolism, 2013, vol. 2, pp. 103-108.
Naik, R. et al., "Latent Autoimmune Diabetes in Adults." The Journal of Clinical Endocrinology and Metabolism, 2009, vol. 94, No. 12, pp. 4635-4644.
National Program for Care Guidelines, "Type 2 Diabetes mellitus." 2002, First Edition, pp. 1-50.
Pearson, E. R. et al., "Variation in TCF7L2 Influences Therapeutic Response to Sulfonylureas." Diabetes, 2007, vol. 56, pp. 2178-2182.
Poudel, Resham R., "Latent autoimmune diabetes of adults: From oral hypoglycemic agents to early insulin." Indian Journal of Endocrinology and Metabolism, 2012, vol. 16, Supplement 1, pp. S41-S46.
Radermecker, Regis et al., "Lipodystrophy Reactions to Insulin." American Journal of Clinical Dermatology, 2007, vol. 8, pp. 21-28.
Sheperd, Todd M. et al., "Efective management of obesity." The Journal of Family Practice, 2003, vol. 52, No. 1, pp. 34-42.
Standl, E. et al., "Diabetes and the Heart." Diabetes Guidelines (DDG), 2002, pp. 1-25.
Suzuki, Y. et al., "Carbon-Carbon Bond Cleavage of a-Hydroxybenzylheteroarenes Catalyzed by Cyanide Ion: Retro-Benzoin Condensation Affords Ketones and Heteroarenes and Benzyl Migration Affords Benzylheteroarenes and Arenecarbaldehydes." Chemical Pharmaceutical Bulletin, 1998, vol. 46(2), pp. 199-206.
Tadayyon, M. et al., "Insulin sensitisation in the treatment of Type 2 diabetes." Expert Opinion Investigative Drugs, 2003, vol. 12, No. 3, pp. 307-324.
Yamagishi, S. et al., "Pleiotropic Effects of Glucagon-like Peptide-1 (GLP-1)-Based Therapies on Vascular Complications in Diabetes." Current Pharmaceutical Design, 2012, vol. 17, pp. 4379-4385.

* cited by examiner

Figure 1: Thermoanalysis of the anhydrous form A/B
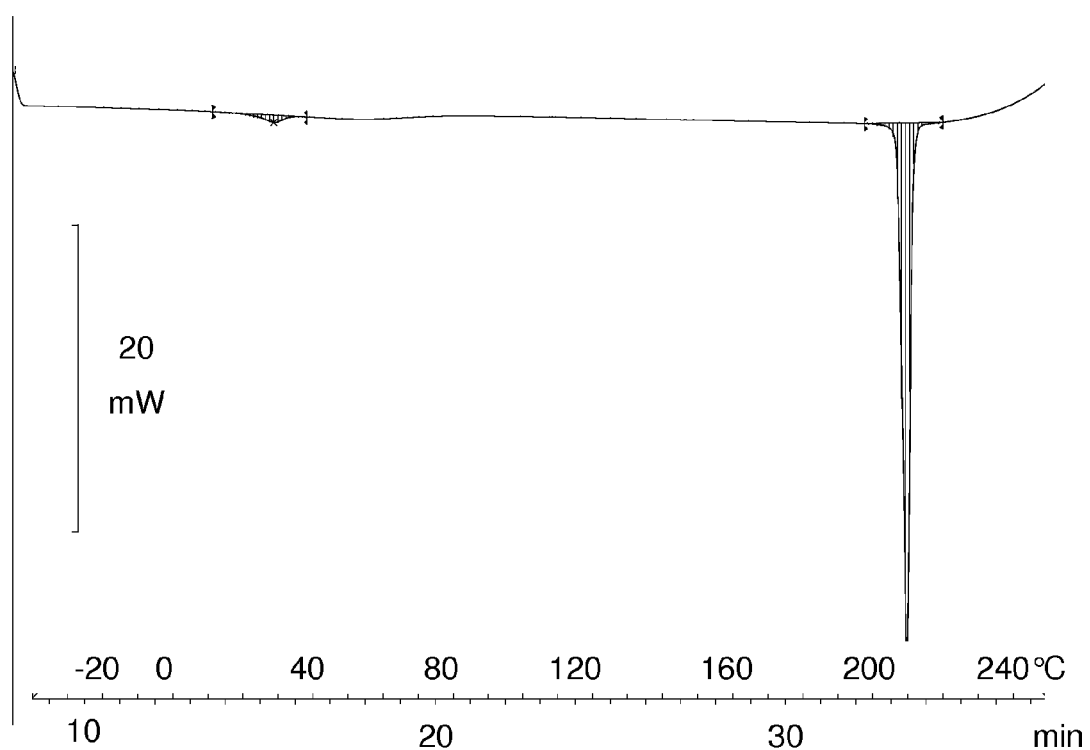

Figure 2: Cyclic DSC diagram of the enantiotropic phase transition
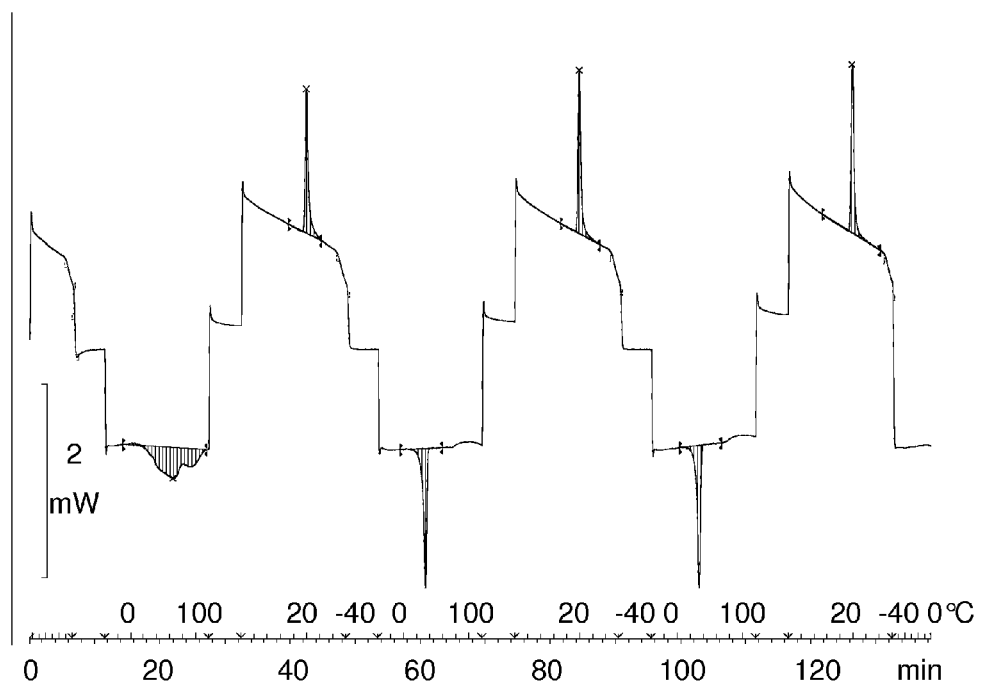

Figure 3: X-ray powder diagram of the anhydrous form A
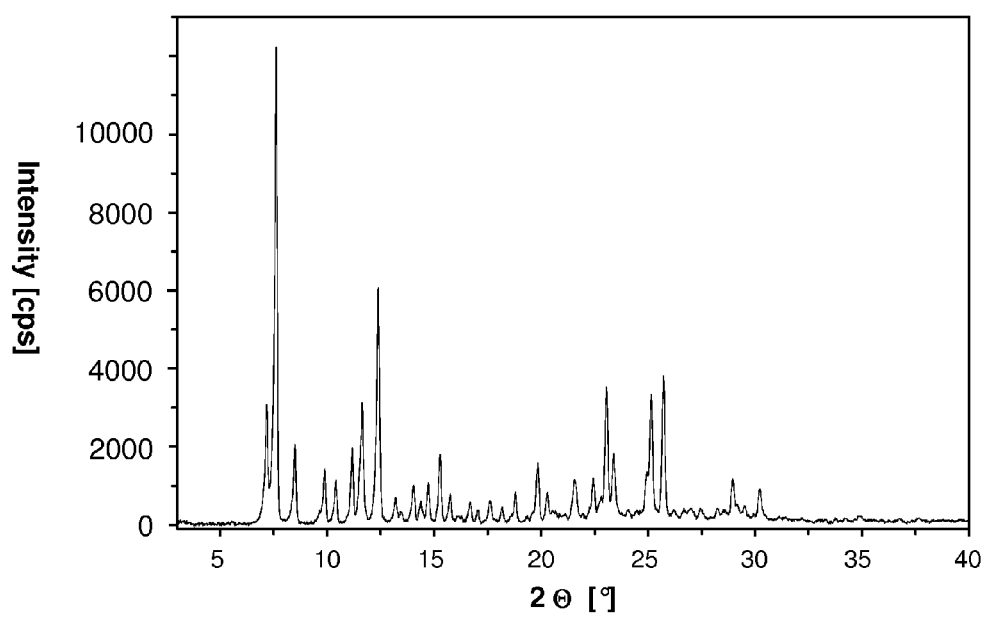

Figure 4: X-ray powder diagram of the anhydrous form B
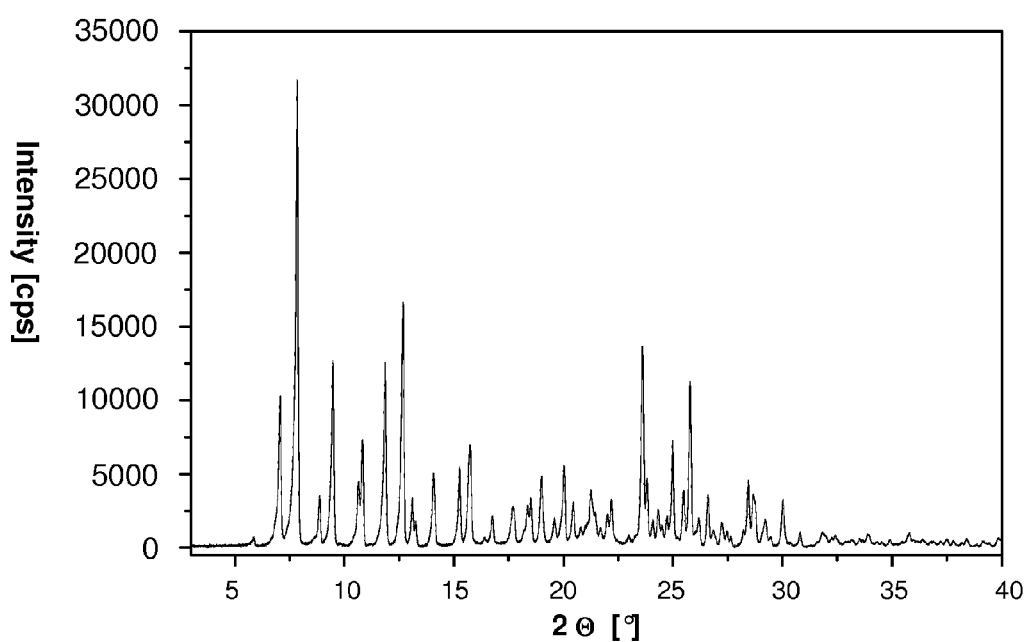

Figure 5: X-ray powder diagram of polymorph C
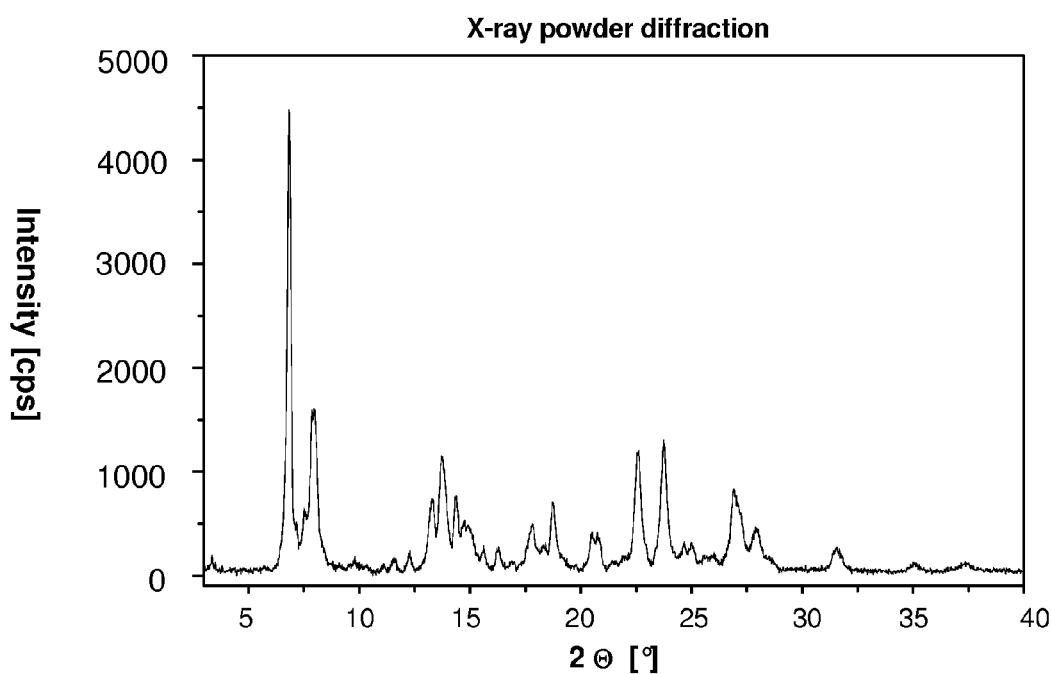

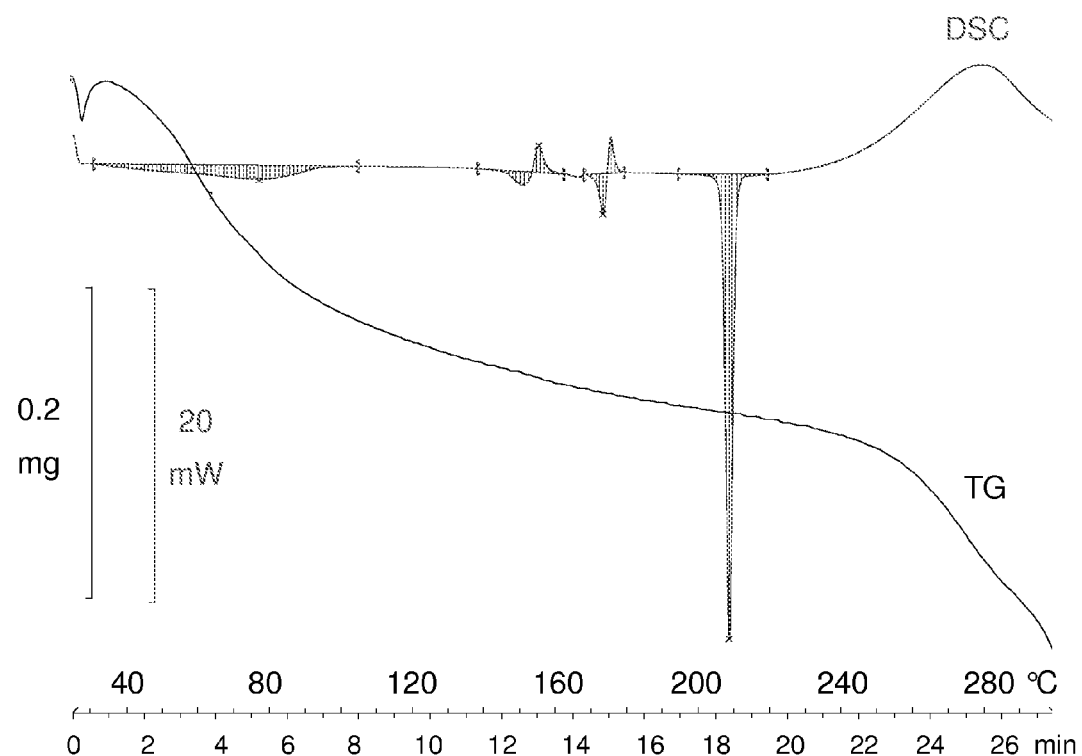
Figure 6: Thermoanalysis of form C

POLYMORPHS

This Application claims priority of EP 06 009 202, which is hereby incorporated by reference in its entirety.

BACKGROUND OF THE INVENTION

1. Field of the Invention

The invention relates to polymorphous crystal modifications of a DPP-IV inhibitor, the preparation thereof and the use thereof for preparing a medicament.

2. Description of the Prior Art

The enzyme DPP-IV, also known by the name CD26, is a serine protease which promotes the cleaving of dipeptides in proteins with a proline or alanine group at the N-terminal end. DPP-IV inhibitors thereby influence the plasma level of bioactive peptides including the peptide GLP-1. Compounds of this type are useful for the prevention or treatment of illnesses or conditions which are associated with an increased DPP-IV activity or which can be prevented or alleviated by reducing the DPP-IV activity, particularly type I or type II diabetes mellitus, prediabetes, or reduced glucose tolerance.

WO 2004/018468 describes DPP-IV inhibitors with valuable pharmacological properties. One example of the inhibitors disclosed therein is 1-[(4-methyl-quinazolin-2-yl)methyl]-3-methyl-7-(2-butyn-1-yl)-8-(3-(R)-amino-piperidin-1-yl)-xanthine.

BRIEF DESCRIPTION OF THE DRAWINGS

FIG. 1 shows the thermoanalysis of the anhydrous form A/B.

FIG. 2 shows a cyclic DSC diagram, in which the phase transition from −40° C. to 120° C. and vice versa has been run through a total of 3 times.

FIG. 3 shows an X-ray powder diagram of the anhydrous form A.

FIG. 4 shows an X-ray powder diagram of the anhydrous form B.

FIG. 5 shows an X-ray powder diagram of polymorph C.

FIG. 6 shows the thermoanalysis of form C.

DETAILED DESCRIPTION OF THE INVENTION

Within the scope of the present invention it has been found that 1-[(4-methyl-quinazolin-2-yl)methyl]-3-methyl-7-(2-butyn-1-yl)-8-(3-(R)-amino-piperidin-1-yl)-xanthine may take on various polymorphous crystal modifications and that the compound prepared in WO 2004/018468 is present at ambient temperature as a mixture of two enantiotropic polymorphs. The temperature at which the two polymorphs transform into one another is 25±15° C. (see FIGS. 1 and 2).

The pure high temperature form (polymorph A), which can be obtained by heating the mixture to temperatures >40° C., melts at 206±3° C. In the X-ray powder diagram (see FIG. 3) this form shows characteristic reflections at the following d values: 11.49 Å, 7.60 Å, 7.15 Å, 3.86 Å, 3.54 Å and 3.47 Å (cf. also Table 1 and 2).

Anhydrous polymorph A may be prepared by
(a) refluxing 1-[(4-methyl-quinazolin-2-yl)methyl]-3-methyl-7-(2-butyn-1-yl)-8-(3-(R)-amino-piperidin-1-yl)-xanthine in absolute ethanol and optionally filtering the mixture,
(b) cooling the hot solution or the hot filtrate until crystallisation sets in,
(c) diluting with a solvent such as tert.-butylmethylether,
(d) suction filtering the solvent mixture and
(e) drying the polymorph A at 45° C. in vacuo.

The low temperature form (polymorph B) is obtained by cooling to temperatures <10° C. In the X-ray powder diagram (see FIG. 4) this form shows characteristic reflections at the following d values: 11.25 Å, 9.32 Å, 7.46 Å, 6.98 Å and 3.77 Å (cf. also Table 3 and 4).

Anhydrous polymorph B may be prepared by
(a) dissolving 1-[(4-methyl-quinazolin-2-yl)methyl]-3-methyl-7-(2-butyn-1-yl)-8-(3-(R)-amino-piperidin-1-yl)-xanthine in absolute ethanol and refluxing and optionally filtering the mixture,
(b) cooling the hot solution or the hot filtrate for crystallisation to a temperature below 10° C.,
(c) diluting with a solvent such as tert.-butylmethylether,
(d) suction filtering the solvent mixture and
(e) drying the polymorph at a temperature below 10° C. in vacuo.

Another polymorph (polymorph C) shows characteristic reflections in the X-ray powder diagram (see FIG. 5) at the following d values: 12.90 Å, 11.10 Å, 6.44 Å, 3.93 Å and 3.74 Å (cf. also Table 5).

Polymorph C is obtained if
(a) 1-[(4-methyl-quinazolin-2-yl)methyl]-3-methyl-7-(2-butyn-1-yl)-8-(3-(R)-amino-piperidin-1-yl)-xanthine is dissolved in methanol and refluxed and optionally filtered in the presence of activated charcoal,
(b) the methanolic solution is cooled to a temperature of 40-60° C.,
(c) a solvent such as tert.-butylmethylether or diisopropylether is added,
(d) the resulting suspension is first of all cooled slowly to 15-25° C. and then later to 0-5° C.,
(e) the crystals formed are suction filtered and washed again with tert.-butylmethylether or diisopropylether and
(f) the crystals thus obtained are dried at a temperature of 70° C. in the vacuum dryer.

Another polymorph (polymorph D) melts at 150±3° C. This polymorph is obtained if polymorph C is heated to a temperature of 30-100° C. or dried at this temperature.

Finally, there is also polymorph E, which melts at a temperature of 175±3° C. Anhydrous polymorph E is formed if polymorph D is melted. On further heating, polymorph E crystallises out of the melt.

The polymorphs thus obtained may be used in the same way as the mixture of the two polymorphs A and B described in WO 2004/018468 for preparing a pharmaceutical composition which is suitable for treating patients with type I and type II diabetes mellitus, prediabetes or reduced glucose tolerance, with rheumatoid arthritis, obesity, or calcitonin-induced osteoporosis, as well as patients in whom an allograft transplant has been carried out. These medicaments contain in addition to one or more inert carriers at least 0.1% to 0.5%, preferably at least 0.5% to 1.5% and particularly preferably at least 1% to 3% of one of the polymorphs A, B, or C.

The following Examples are intended to illustrate the invention in more detail.

Example 1

Crystallisation of Polymorph A

Crude 1-[(4-methyl-quinazolin-2-yl)methyl]-3-methyl-7-(2-butyn-1-yl)-8-(3-(R)-amino-piperidin-1-yl)-xanthine is refluxed with 5 times as much absolute ethanol and the hot solution is filtered clear through activated charcoal. After the filtrate has been cooled to 20° C. and crystallisation has set in, the solution is diluted to double the volume with tert.-butylmethylether. Then the suspension is cooled to 2° C., stirred for 2 hours, suction filtered and dried in the vacuum dryer at 45° C.

FIG. 1 shows the thermoanalysis of the anhydrous form A/B.

Plymorph A melts at 206±3° C. In the DSC diagram another slightly endothermic signal can be seen at approx. 25° C. This is a fully reversible solid-solid phase transition between the two enantiotropic crystal modifications A and B. The form A is the thermodynamically stable modification above this transformation temperature, w| form B is the thermodynamically stable modification below this transformation temperature.

FIG. 2 shows a cyclic DSC diagram, in which the phase transition from −40° C. to 120° C. and vice versa has been run through a total of 3 times. During heating, the phase transition is observed as an endothermic signal and, correspondingly, during cooling it is observed as an exothermic signal. During the first heating cycle the phase transition may also be observed as an endothermic double signal or as a very broad signal while in all the other cycles the signal occurs as a very sharp endothermic or exothermic signal, depending on whether heating or cooling is taking place.

FIG. 3 shows an X-ray powder diagram of the anhydrous form A

TABLE 1

Labelled X-ray reflexes up to 30 ° 2Θ with intensities (standardised) for the anhydrous polymorph A

| 2Θ [°] | intensity I/I$_o$ [%] | d$_{hkl}$ [Å] | h | k | l | d$_{exp-calc}$ [Å] |
|---|---|---|---|---|---|---|
| 5.56 | 1 | 15.89 | 1 | 0 | 0 | −0.008 |
| 7.18 | 32 | 12.31 | 0 | 1 | 1 | 0.005 |
| 7.62 | 100 | 11.59 | 1 | 1 | 0 | 0.007 |
| 8.49 | 20 | 10.41 | −1 | 1 | 1 | 0.002 |
| 9.91 | 24 | 8.92 | 0 | 0 | 2 | 0.003 |
| 10.41 | 18 | 8.49 | 0 | 2 | 0 | 0.024 |
| 11.18 | 24 | 7.91 | 2 | 0 | 0 | 0.038 |
| 11.63 | 41 | 7.60 | −1 | 1 | 2 | 0.003 |
| 12.37 | 59 | 7.15 | −1 | 2 | 1 | −0.003 |
| 13.19 | 6 | 6.71 | 1 | 2 | 1 | −0.014 |
| 13.45 | 3 | 6.58 | −2 | 0 | 2 | 0.007 |
| 14.05 | 6 | 6.30 | 2 | 1 | 1 | 0.011 |
| 14.38 | 6 | 6.16 | 0 | 2 | 2 | 0.003 |
| 14.71 | 10 | 6.02 | −1 | 2 | 2 | −0.008 |
| 15.26 | 13 | 5.80 | 2 | 2 | 0 | 0.001 |
| 15.76 | 10 | 5.62 | −1 | 1 | 3 | 0.008 |
| 16.09 | 1 | 5.51 | 1 | 2 | 2 | −0.010 |
| 16.32 | 1 | 5.43 | 2 | 0 | 2 | 0.035 |
| 16.69 | 4 | 5.31 | 2 | 2 | 1 | −0.007 |
| 17.03 | 3 | 5.20 | −1 | 3 | 1 | 0.026 |
| 17.63 | 6 | 5.03 | 1 | 3 | 1 | 0.006 |
| 18.17 | 5 | 4.88 | −1 | 2 | 3 | −0.004 |
| 18.78 | 7 | 4.72 | −1 | 3 | 2 | −0.014 |
| 19.30 | 1 | 4.60 | −2 | 3 | 1 | −0.019 |
| 19.61 | 2 | 4.52 | −3 | 2 | 1 | 0.036 |
| 19.86 | 20 | 4.47 | −2 | 2 | 3 | 0.040 |
| 20.29 | 10 | 4.37 | 2 | 0 | 3 | 0.019 |
| 20.57 | 4 | 4.31 | 0 | 1 | 4 | 0.006 |
| 21.12 | 1 | 4.20 | 3 | 0 | 2 | 0.048 |
| 21.57 | 12 | 4.12 | −2 | 1 | 4 | 0.028 |
| 22.46 | 10 | 3.96 | 1 | 4 | 1 | 0.035 |
| 23.03 | 35 | 3.86 | 4 | 1 | 0 | 0.022 |
| 23.39 | 21 | 3.80 | −1 | 4 | 2 | 0.019 |
| 24.08 | 2 | 3.69 | −3 | 1 | 4 | −0.006 |
| 24.51 | 1 | 3.63 | −4 | 0 | 3 | 0.036 |
| 24.91 | 10 | 3.57 | −2 | 4 | 2 | 0.003 |
| 25.14 | 39 | 3.54 | 3 | 1 | 3 | 0.043 |
| 25.69 | 36 | 3.47 | −3 | 3 | 3 | 0.041 |
| 26.68 | 3 | 3.34 | 0 | 5 | 1 | 0.035 |
| 26.90 | 2 | 3.31 | 3 | 4 | 0 | 0.027 |
| 27.10 | 2 | 3.29 | 0 | 2 | 5 | 0.030 |
| 27.42 | 3 | 3.25 | 4 | 3 | 0 | 0.006 |
| 28.19 | 2 | 3.16 | −1 | 5 | 2 | −0.035 |
| 28.54 | 2 | 3.12 | 3 | 0 | 4 | 0.047 |
| 28.94 | 11 | 3.08 | 0 | 4 | 4 | −0.036 |
| 29.18 | 5 | 3.06 | −4 | 3 | 3 | 0.017 |
| 29.50 | 4 | 3.03 | −1 | 0 | 6 | 0.041 |
| 30.18 | 7 | 2.96 | −1 | 5 | 3 | −0.042 |

TABLE 2

Lattice metrics of the anhydrous form A

| | |
|---|---|
| Symmetry: | monocline |
| space group: | P |
| a: | 16.16(2) Å |
| b: | 17.02(1) Å |
| c: | 18.18(2) Å |
| β: | 100.95(6)° |
| cell volume: | 4907(11) Å$^3$ |

Example 2

Crystallisation of Polymorph B

Polymorph B is obtained by cooling form A from Example 1 to temperatures <10° C.

FIG. 4 shows an X-ray powder diagram of the anhydrous form B

TABLE 3

Labelled X-ray reflexes up to 30 ° 2Θ with intensities (standardised) for the anhydrous form B

| 2Θ [°] | intensity I/I$_o$ [%] | d$_{hkl}$ [Å] | h | k | l | d$_{exp-calc}$ [Å] |
|---|---|---|---|---|---|---|
| 5.82 | 3 | 15.17 | 1 | 0 | 0 | −0.007 |
| 7.04 | 33 | 12.55 | 0 | 1 | 1 | 0.001 |
| 7.82 | 100 | 11.3 | 1 | 1 | 0 | −0.004 |
| 8.84 | 11 | 10 | −1 | 1 | 1 | 0.001 |
| 9.44 | 40 | 9.36 | 1 | 1 | 1 | 0.011 |
| 10.62 | 14 | 8.32 | −1 | 0 | 2 | 0.013 |
| 10.79 | 24 | 8.19 | 0 | 1 | 2 | −0.005 |
| 11.82 | 39 | 7.48 | −1 | 1 | 2 | −0.003 |
| 12.64 | 53 | 7 | −1 | 2 | 1 | −0.009 |
| 13.07 | 11 | 6.77 | 1 | 2 | 1 | −0.006 |
| 13.24 | 6 | 6.68 | −2 | 1 | 1 | 0.004 |
| 14.04 | 16 | 6.3 | 2 | 1 | 1 | 0.003 |
| 15.23 | 17 | 5.81 | −2 | 1 | 2 | 0.003 |
| 15.70 | 22 | 5.64 | 2 | 2 | 0 | 0.016 |
| 16.38 | 2 | 5.41 | 0 | 3 | 1 | −0.010 |
| 16.73 | 6 | 5.3 | 2 | 2 | 1 | 0.008 |
| 17.67 | 8 | 5.02 | 0 | 2 | 3 | 0.014 |
| 18.16 | 3 | 4.88 | −1 | 2 | 3 | 0.005 |
| 18.33 | 9 | 4.84 | 3 | 1 | 0 | 0.016 |
| 18.48 | 10 | 4.8 | −3 | 1 | 1 | −0.003 |
| 18.97 | 15 | 4.68 | 0 | 0 | 4 | −0.001 |
| 19.56 | 6 | 4.54 | 1 | 3 | 2 | 0.013 |
| 20.00 | 17 | 4.44 | 2 | 1 | 3 | 0.000 |
| 20.42 | 9 | 4.35 | 1 | 0 | 4 | 0.009 |
| 20.76 | 4 | 4.27 | 3 | 0 | 2 | −0.014 |
| 20.97 | 4 | 4.23 | 0 | 4 | 0 | 0.010 |
| 21.07 | 5 | 4.21 | 1 | 1 | 4 | −0.009 |

TABLE 3-continued

Labelled X-ray reflexes up to 30 ° 2 Θ with intensities (standardised) for the anhydrous form B

| 2 Θ [°] | intensity I/I$_o$ [%] | d$_{hkl}$ [Å] | h | k | l | d$_{exp-calc}$ [Å] |
|---|---|---|---|---|---|---|
| 21.22 | 12 | 4.18 | 0 | 3 | 3 | 0.001 |
| 21.40 | 7 | 4.15 | 3 | 2 | 1 | 0.004 |
| 21.66 | 4 | 4.1 | −1 | 3 | 3 | 0.018 |
| 21.98 | 7 | 4.04 | 2 | 2 | 3 | −0.003 |
| 22.16 | 10 | 4.01 | −3 | 1 | 3 | 0.008 |
| 22.97 | 3 | 3.87 | 1 | 2 | 4 | −0.006 |
| 23.58 | 43 | 3.77 | −2 | 3 | 3 | −0.003 |
| 23.78 | 15 | 3.74 | −2 | 2 | 4 | −0.004 |
| 24.05 | 6 | 3.7 | 4 | 1 | 0 | −0.002 |
| 24.29 | 8 | 3.66 | −2 | 4 | 1 | −0.008 |
| 24.46 | 5 | 3.64 | 3 | 3 | 1 | 0.018 |
| 24.71 | 7 | 3.6 | 0 | 3 | 4 | 0.001 |
| 24.96 | 23 | 3.56 | 2 | 3 | 3 | −0.001 |
| 25.45 | 12 | 3.5 | −2 | 4 | 2 | −0.010 |
| 25.75 | 35 | 3.46 | 4 | 2 | 0 | 0.011 |
| 25.99 | 4 | 3.43 | 3 | 2 | 3 | 0.014 |
| 26.15 | 6 | 3.41 | 3 | 3 | 2 | 0.010 |
| 26.57 | 12 | 3.35 | −2 | 3 | 4 | −0.001 |
| 26.82 | 4 | 3.32 | −3 | 2 | 4 | 0.011 |
| 27.20 | 6 | 3.28 | 1 | 2 | 5 | −0.010 |
| 27.43 | 4 | 3.25 | −2 | 4 | 3 | −0.003 |
| 27.60 | 3 | 3.23 | −2 | 2 | 5 | −0.005 |
| 28.19 | 4 | 3.16 | 3 | 4 | 1 | 0.010 |
| 28.40 | 15 | 3.14 | 0 | 4 | 4 | −0.013 |
| 28.64 | 12 | 3.11 | 0 | 0 | 6 | 0.016 |
| 29.18 | 6 | 3.06 | −4 | 3 | 2 | 0.004 |
| 29.42 | 2 | 3.03 | 1 | 4 | 4 | 0.002 |
| 29.99 | 10 | 2.98 | 0 | 5 | 3 | −0.008 |
| 30.77 | 3 | 2.9 | −4 | 3 | 3 | 0.018 |

TABLE 4

Lattice metrics of the anhydrous form B

| Symmetry: | monocline |
|---|---|
| space group: | P2$_1$/c (# 14) |
| a: | 15.23(1) Å |
| b: | 16.94(1) Å |
| c: | 18.79(1) Å |
| β: | 95.6(2)° |
| cell volume: | 4823(3) Å$^3$ |

Example 3

Crystallisation of Polymorph C

Crude 1-[(4-methyl-quinazolin-2-yl)methyl]-3-methyl-7-(2-butyn-1-yl)-8-(3-(R)-amino-piperidin-1-yl)-xanthine (26 kg) is refluxed with 157 l methanol, combined with 1.3 kg of activated charcoal and after 30 minutes' stirring the mixture is filtered and rinsed with 26 l methanol. 122 l of methanol are distilled off from the filtrate, then the residue is cooled to 45-55° C. 52 l of tert.-butylmethylether are added to the residue over 30 minutes. Then the mixture is stirred for another 60 minutes at 45-55° C. Crystallisation takes place within this time. A further 78 l tert. butylmethylether are added to the suspension over 30 minutes and then it is stirred again for a further 60 minutes at 45-55° C. It is diluted to four times the volume. The suspension is slowly cooled to 15-25° C. and stirred overnight at this temperature. After the suspension has been cooled to 0-5° C. the crystals are suction filtered, washed with 2 batches tert.-butylmethylether and dried at 70° C. in the vacuum dryer.

FIG. 5 shows an X-ray powder diagram of polymorph C

TABLE 5

X-ray reflexes up to 30° 2 Θ with intensities (standardised) for the anhydrous form C

| 2 Θ [°] | d$_{hkl}$ [Å] | intensity I/I$_o$ [%] |
|---|---|---|
| 3.38 | 26.16 | 4 |
| 6.85 | 12.90 | 100 |
| 7.18 | 12.31 | 11 |
| 7.52 | 11.74 | 14 |
| 7.96 | 11.10 | 36 |
| 9.80 | 9.02 | 3 |
| 11.11 | 7.96 | 2 |
| 11.58 | 7.64 | 3 |
| 12.30 | 7.19 | 5 |
| 13.30 | 6.65 | 16 |
| 13.75 | 6.44 | 26 |
| 14.38 | 6.16 | 17 |
| 14.74 | 6.01 | 11 |
| 14.95 | 5.92 | 10 |
| 15.63 | 5.66 | 6 |
| 16.28 | 5.44 | 5 |
| 17.81 | 4.98 | 10 |
| 18.33 | 4.83 | 6 |
| 18.75 | 4.73 | 15 |
| 20.51 | 4.33 | 8 |
| 20.77 | 4.27 | 8 |
| 21.47 | 4.14 | 3 |
| 21.96 | 4.05 | 4 |
| 22.59 | 3.93 | 26 |
| 23.76 | 3.74 | 29 |
| 24.68 | 3.60 | 6 |
| 25.01 | 3.56 | 7 |
| 25.57 | 3.48 | 4 |
| 25.96 | 3.43 | 4 |
| 26.93 | 3.31 | 18 |
| 27.22 | 3.27 | 13 |
| 27.92 | 3.19 | 10 |

Example 4

Crystallisation of Polymorph D

Polymorph D is obtained if polymorph C from Example 3 is heated to a temperature of 30-100° C. or dried at this temperature.

Example 5

Crystallisation of Polymorph E

Anhydrous polymorph E is obtained if polymorph D is melted. On further heating, polymorph E crystallises out of the melt.

FIG. 6 shows a thermoanalysis of form C

In the DSC diagram of form C a whole range of signals can be observed. The strongest signal is the melting point of the anhydrous form A at approx. 206° C., which is produced in the DSC experiment. Before the melting point a number of other endothermic and exothermic signals can be observed. Thus, for example, a very broad and weak endothermic signal can be seen between 30 and 100° C., which correlates with the main loss of weight in thermogravimetry (TR). A TG/IR coupling experiment provides the information that only water escapes from the sample in this temperature range.

An X-ray powder diagram taken of a sample maintained at a temperature of 100° C. shows different X-ray reflections from the starting material, suggesting that form C is a hydrate phase with stoichiometry somewhere in the region of a hemihydrate or monohydrate. The temperature-controlled sample is another anhydrous modification D, which only stable under anhydrous conditions. The D form melts at approx. 150° C. Another anhydrous crystal modification E crystallises from the melt, and when heated further melts at approx. 175° C. Finally, form A crystallises from the melt of form E. Form E is also a metastable crystal modification which occurs only at high temperatures.

The invention claimed is:

1. A method of preparing an anhydrous polymorph A of the compound 1-[(4-methyl-quinazolin-2-yl)methyl]-3-methyl-7-(2-butyn-1-yl)-8-(3-(R)-amino-piperidin-1-yl)-xanthine, the method comprising:
   (a) dissolving 1-[(4-methyl-quinazolin-2-yl)methyl]-3-methyl-7-(2-butyn-1-yl)-8-(3-(R)-amino-piperidin-1-yl)-xanthine in absolute ethanol to provide a solution;
   (b) refluxing the solution to provide a hot solution and, optionally filtering the hot solution to provide a hot filtrate,
   (c) cooling the hot solution or the hot filtrate until crystallisation sets in,
   (d) diluting the cooled solution or the cooled filtrate with a solvent to provide a solvent mixture,
   (e) suction filtering the solvent mixture, and
   (f) drying the solids collected by filtration at 45° C. in vacuo to provide said anhydrous polymorph A; wherein said anhydrous polymorph A melts at 206±3° C., and said anhydrous polymorph A exhibits an X-ray powder diagram having characteristic reflections at the following d values: 11.59 Å, 7.60 Å, 7.15 Å, 3.86 Å, 3.54 Å and 3.47 Å.

2. The method of claim 1, wherein the solvent used in Step (d) is tertiary-butylmethylether.

3. The method according to claim 1, wherein anhydrous polymorph A has an X-ray powder diagram as shown in FIG. 3.

4. The method of claim 1, further characterized in that the reflection at 11.59 Å in the X-ray powder diagram has a relative intensity of 100% and further characterized in that the X-ray powder diagram exhibits no reflections having a relative intensity of 1% or more at the following d values: 11.3 Å, 9.36 Å, 7.48 Å, and 7 Å.

5. The method according to claim 1, wherein polymorph A is characterised by its lattice metrics:

| Symmetry: | monoclinic |
|---|---|
| space group: | P |
| a: | 16.16(2) Å |
| b: | 17.02(1) Å |
| c: | 18.18(2) Å |
| β: | 100.95(6)° |
| cell volume: | 4907(11) Å³. |

6. A method of preparing anhydrous polymorph B of the compound 1-[(4-methyl-quinazolin-2-yl)methyl]-3-methyl-7-(2-butyn-1-yl)-8-(3-(R)-amino-piperidin-1-yl)-xanthine, the method comprising:
   (a) dissolving 1-[(4-methyl-quinazolin-2-yl)methyl]-3-methyl-7-(2-butyn-1-yl)-8-(3-(R)-amino-piperidin-1-yl)-xanthine in absolute ethanol to provide a solution,
   (b) refluxing the solution to provide a hot solution and, optionally filtering the hot solution to provide a hot filtrate,
   (c) cooling the hot solution or the hot filtrate for crystallisation to a temperature below 10° C. to provide a cold solution or cold filtrate,
   (d) diluting the cold solution or cold filtrate with a solvent to provide a solvent mixture,
   (e) suction filtering the solvent mixture, and
   (f) drying the collected solids at a temperature below 10° C. in vacuo to provide anhydrous polymorph B;
   or
   cooling polymorph A or a mixture of polymorphs A and B to temperatures <10° C.; wherein
      said anhydrous polymorph B transforms reversibly into the polymorph A of claim 1 at temperature of 10-40° C., and
      said anhydrous polymorph B exhibits an X-ray powder diagram having characteristic reflections at the following d values: 11.3 Å, 9.36 Å, 7.48 Å, 7 Å and 3.77 Å.

7. The method of claim 6, wherein the solvent in Step (d) is tertiary-butylmethylether.

8. The method according to claim 6 wherein anhydrous polymorph B has an X-ray powder diagram as shown in FIG. 4.

9. The method of claim 6, further characterized in that the reflection at 11.3 Å in the X-ray powder diagram has a relative intensity of 100% and further characterized in that the X-ray powder diagram exhibits no reflections having a relative intensity of 1% or more at the following d values: 11.59 Å, 7.60 Å, and 7.15 Å.

10. The method according to claim 6, wherein polymorph B is characterised by its lattice metrics:

| Symmetry: | monoclinic |
|---|---|
| space group: | P2₁/c (# 14) |
| a: | 15.23(1) Å |
| b: | 16.94(1) Å |
| c: | 18.79(1) Å |
| β: | 95.6(2)° |
| cell volume: | 4823(3) Å³. |

11. A method of preparing a medicament, the method comprising
   i) preparing the anhydrous polymorph A by the method of claim 1, and
   ii) combining the anhydrous polymorph A with one or more inert carriers to provide a medicament containing 0.1% to 0.5%, or 0.5% to 1.5%, or 1% to 3% of the anhydrous polymorph A based on the total weight of the polymorph A and the one or more inert carriers.

12. A method of preparing a medicament, the method comprising
   i) preparing the anhydrous polymorph B by the method of claim 6, and
   ii) combining the anhydrous polymorph B with one or more inert carriers to provide a medicament containing 0.1% to 0.5%, or 0.5% to 1.5%, or 1% to 3% of the anhydrous polymorph B based on the total weight of the polymorph B and the one or more inert carriers.

* * * * *